(12) United States Patent
Akiyoshi

(10) Patent No.: US 12,065,675 B2
(45) Date of Patent: Aug. 20, 2024

(54) SELECTION METHOD OF iPS CELL, PREPARATION METHOD OF iPS CELL, AND CONTROL DEVICE

(71) Applicant: OLYMPUS CORPORATION, Tokyo (JP)

(72) Inventor: Ryutaro Akiyoshi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 526 days.

(21) Appl. No.: 17/464,024

(22) Filed: Sep. 1, 2021

(65) Prior Publication Data

US 2022/0041995 A1 Feb. 10, 2022

Related U.S. Application Data

(63) Continuation of application No. PCT/JP2019/009194, filed on Mar. 7, 2019.

(51) Int. Cl.
*C12N 5/074* (2010.01)
*C12M 1/34* (2006.01)
(Continued)

(52) U.S. Cl.
CPC ........... *C12N 5/0696* (2013.01); *C12M 35/02* (2013.01); *C12M 41/46* (2013.01); *C12N 15/85* (2013.01);
(Continued)

(58) Field of Classification Search
CPC .............. C12N 5/0696; C12N 2501/60; C12N 2501/602; C12N 2501/603; C12N 2501/604; C12N 2501/606; C12N 2501/608; C12N 15/85; C12N 2800/108; C12M 35/02; C12M 41/46; C12Q 1/66; G01N 21/6428; G01N 2021/6439
See application file for complete search history.

(56) References Cited

U.S. PATENT DOCUMENTS

| 10,544,396 B2 * | 1/2020 | Yuasa ................. C12N 5/0696 |
| 2019/0352727 A1 | 11/2019 | Akiyoshi |
| 2020/0158719 A1 | 5/2020 | Akiyoshi |

FOREIGN PATENT DOCUMENTS

| WO | 2018/092321 A1 | 5/2018 |
| WO | 2018/122932 A1 | 7/2018 |
| WO | 2019/021472 A1 | 1/2019 |

OTHER PUBLICATIONS

Yamanaka, et al. Computer English Translation, pp. 1-19 (Year: 2011).*

(Continued)

*Primary Examiner* — Daniel G Mariam
(74) *Attorney, Agent, or Firm* — Scully, Scott, Murphy & Presser, P.C.

(57) ABSTRACT

A selection method of an iPS cell includes: at a reprogramming process to culture a cell including a plurality of combinations of initializing factors labelled with luminescent genes that are different with each other, acquiring a photon number per unit area or a photon number per unit time of each of the luminescent genes of the cell; judging whether the acquired photon number is more than a threshold that is predetermined for the acquired photon number; and when the acquired photon number is more than the threshold, selecting this cell as an objective cell for a next process.

17 Claims, 12 Drawing Sheets

Specification includes a Sequence Listing.

(51) Int. Cl.
  *C12M 1/42* (2006.01)
  *C12N 15/85* (2006.01)
  *C12Q 1/66* (2006.01)
  *G01N 21/64* (2006.01)

(52) U.S. Cl.
  CPC .......... *C12Q 1/66* (2013.01); *G01N 21/6428* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2800/108* (2013.01); *G01N 2021/6439* (2013.01)

(56) References Cited

OTHER PUBLICATIONS

International Search Report dated Jun. 4, 2019 received in PCT/JP2019/009194.
Donai, Kenichiro, et al., "Establishment of a reporter system to monitor silencing status in induced pluripotent stem cell lines", Analytical Biochemistry, 2013, vol. 443, pp. 104-112.
Teshigawara, Rika, et al., non-official translation (Following reprogramming to human iPS cells—Multicolor fluorescence analysis system-, The 41st Annual meeting Program of Molecular Biology Society of Japan), 2018, 2P-0443.
Papapetrou, Eirini P., et al. "Stoichiometric and temporal requirements of Oct4, Sox2, Klf4, and c-Myc expression for efficient human IPSC induction and differentiation", PNAS, 2009, vol. 106, No. 31, pp. 12759-12764.

\* cited by examiner

SELECTION METHOD OF iPS CELL, PREPARATION METHOD OF iPS CELL, AND CONTROL DEVICE

CROSS-REFERENCE TO RELATED APPLICATION

This application is a continuation of International Application No. PCT/JP2019/009194, filed on Mar. 7, 2019, the entire contents of which are incorporated herein by reference.

INCORPORATION BY REFERENCE OF SEQUENCE LISTING

The Sequence Listing in the ASCII text file, named as 40016Z SequenceListing.txt of 6 KB bytes, created on Oct. 5, 2021, and submitted to the United States Patent and Trademark Office via EFS-Web, is incorporated herein by reference.

BACKGROUND

1. Technical Field

The present disclosure relates to a selection method of an iPS cell, a preparation method of an iPS cell, and a control device.

2. Related Art

An iPS (induced Pluripotent Stem) cell is induced after introducing a plurality of genes that are necessary for initialization (initializing factors), typically represented by Yamanaka factors (for example, Oct4, Sox2, Klf4, and c-myc), into a cell followed by culturing for a prescribed culture period. The initialization process of a cell is called a reprogramming process. Selection of the iPS cell in the reprogramming process is important for selection of a good iPS cell. It is expected that efficient selection of a good iPS cell can lead to smooth differentiation to various organs and the like for regenerative medicine thereafter.

For this, a technology of selection of the iPS cell is proposed as follows. Namely, at the reprogramming process, the luminescence amount of a luminescent gene (luminescent protein) that emits the same expression amount with the Yamanaka factor is chronologically analyzed so as to quantify the difference in the chronological variation pattern of the expression pattern of each factor thereby objectively judging the iPS cell from the colonies having good shapes (for example, see International Publication No. 2018-092321).

There is also a known technology to properly grow the iPS cell by analyzing an optimum amount of the Yamanaka factor that is going to be introduced into a cell at the reprogramming process (for example, see "Stoichiometric and temporal requirements of Oct4, Sox2, Klf4, and c-Myc expression for efficient human iPSC induction and differentiation", PNAS, 2009, Vol. 106, No. 31, pp. 12579-12764.

SUMMARY

In some embodiments, a selection method of an iPS cell includes: at a reprogramming process to culture a cell including a plurality of combinations of initializing factors labelled with luminescent genes that are different with each other, acquiring a photon number per unit area or a photon number per unit time of each of the luminescent genes of the cell; judging whether the acquired photon number is more than a threshold that is predetermined for the acquired photon number; and when the acquired photon number is more than the threshold, selecting this cell as an objective cell for a next process.

In some embodiments, a preparation method of an iPS cell includes: at a reprogramming process to culture a cell including a plurality of combinations of initializing factors labelled with luminescent genes that are different with each other, acquiring a luminescence amount of each of the luminescent genes of the cell; judging whether the acquired luminescence amount is more than a threshold that is predetermined for the acquired luminescence amount; when the acquired luminescence amount is more than the threshold, selecting this cell as an objective cell for a next process; and transplanting the selected cell to a new culture vessel, repeatedly up to a prescribed number of times.

In some embodiments, a control device includes a processor comprising hardware, the processor being configured to: acquire, at a reprogramming process to culture a cell including a plurality of combinations of initializing factors labelled with luminescent genes that are different with each other, a photon number per unit area or a photon number per unit time of each of the luminescent genes of the cell; judge whether the acquired photon number is more than a threshold that is predetermined for the acquired photon number; and when the acquired photon number is more than the threshold, select this cell as an objective cell for a next process.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
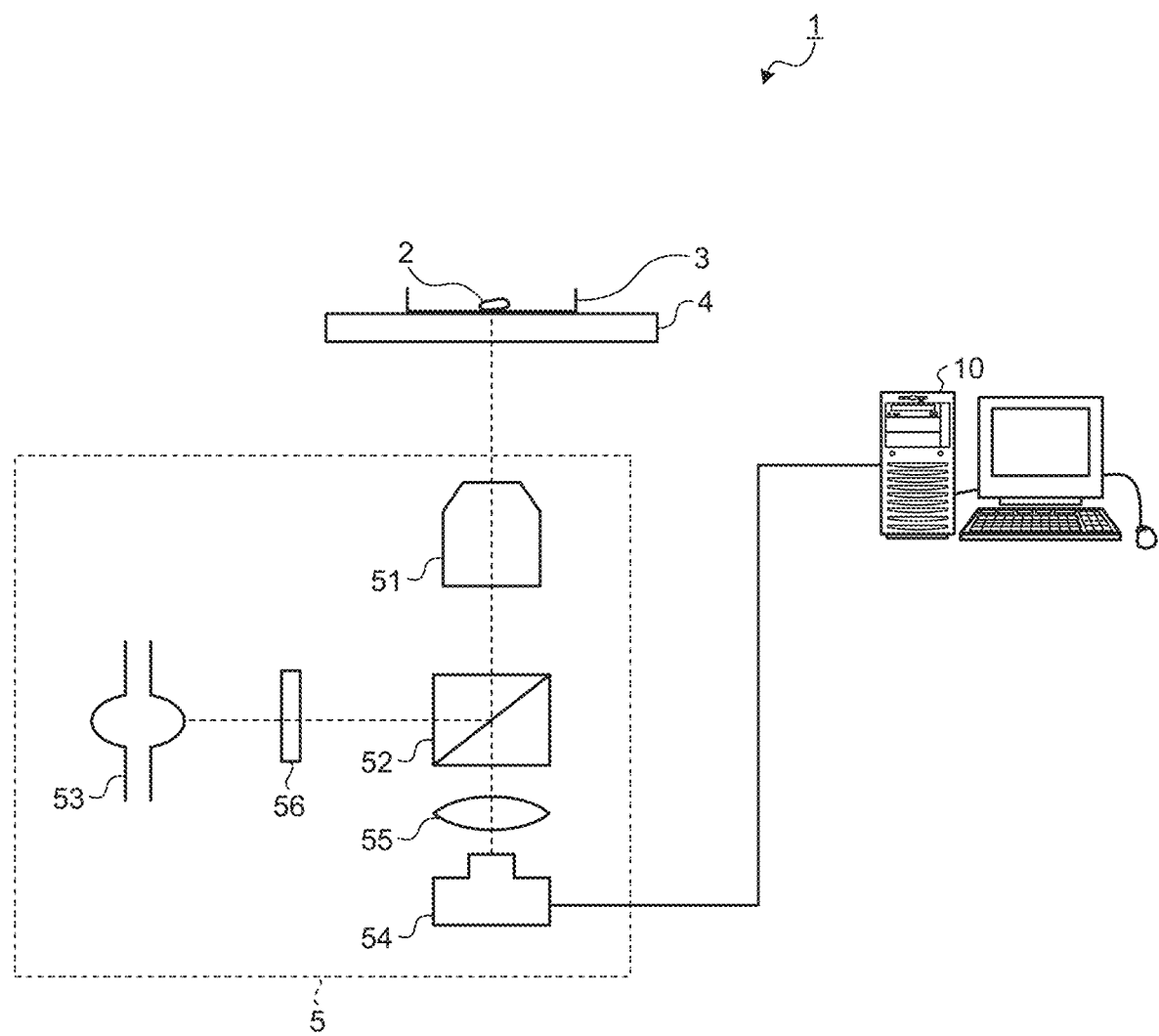
FIG. 1 is a drawing illustrating one example of the entire composition of the selection system of the iPS cell according to a first embodiment of the disclosure.

Hereinafter, with referring to the drawings, the explanation will be made as to the selection method of the iPS cell and preparation method of the iPS cell according to the embodiments of the disclosure. Note that the disclosure is not restricted by these embodiments. In the description in the drawings, the same symbols are attached to the respective corresponding portions.

First Embodiment

Figure 2:
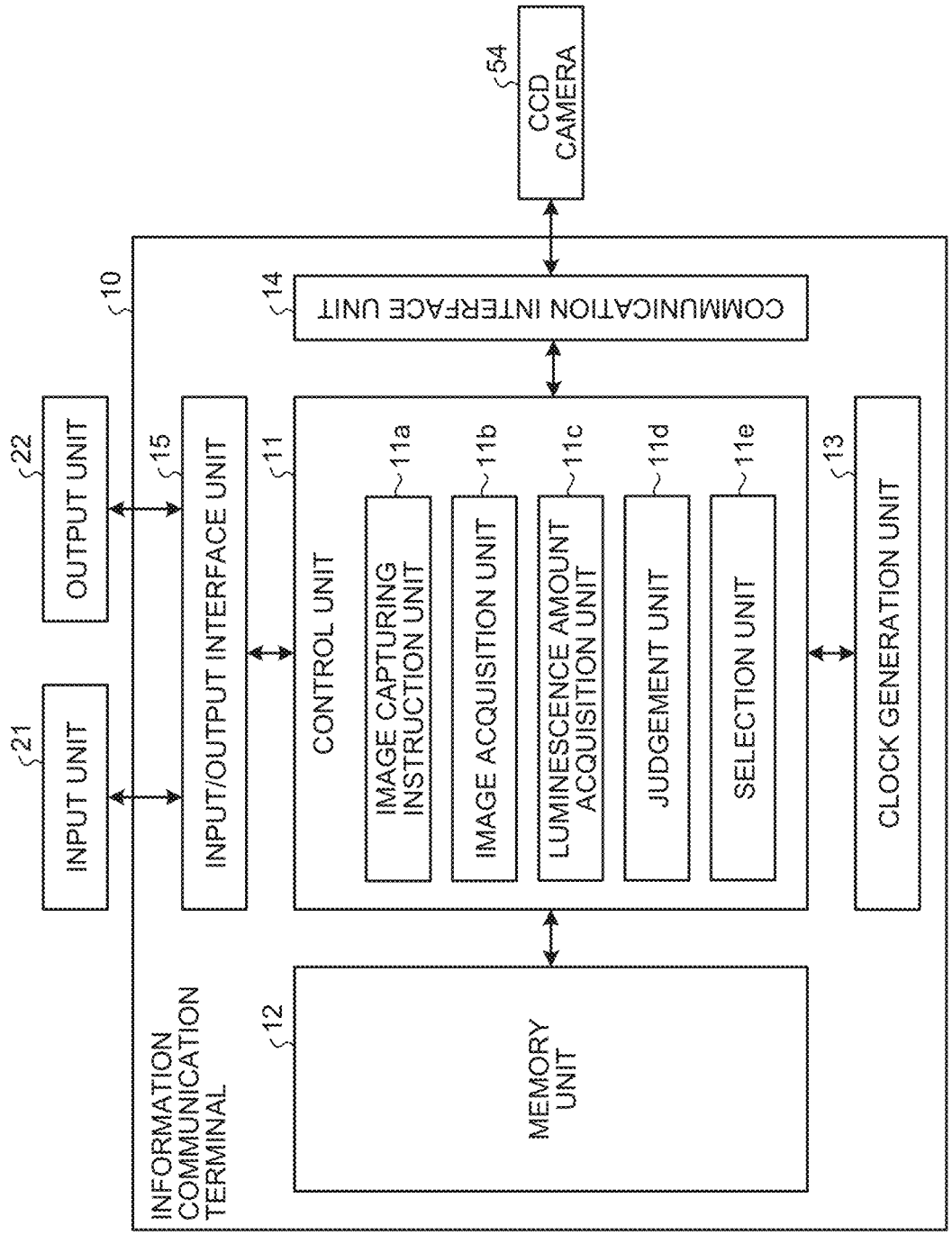
FIG. 2 is a block diagram illustrating the functional composition of the information communication terminal in the selection system of the iPS cell according to the first embodiment of the disclosure.

FIG. 1 is the drawing illustrating one example of the entire composition of the selection system of the iPS cell according to the first embodiment of the disclosure. FIG. 2 is the block diagram illustrating the functional composition of the information communication terminal in the selection system of the iPS cell according to the first embodiment of the disclosure. A selection system 1 according to the first embodiment of the disclosure is the system to select the iPS cell that is suitable for differentiation to various organs on the basis of a plurality of images acquired by imaging the light from the sample.

As illustrated in FIG. 1, the selection system 1 is provided with a sample 2, a vessel 3 that accommodates the sample 2, a stage 4 on which the vessel 3 is disposed, an imaging unit 5, and an information communication terminal 10.

The sample 2 is, for example, the cell that is introduced with "nucleic acids encoding more than one kind of initializing factors that are necessary for reprogramming of a somatic cell" and "nucleic acids encoding a luminescent reporter protein (hereinafter, this is also called a luminescent protein) that is configured so as to express with at least one of more than one kind of the initializing factors". Specifically, the sample 2 is the somatic cell that is introduced with the nucleic acids encoding more than one kind of the initializing factors (transcription factors such as Oct3/4, Klf4, Sox2, L-myc, and LIN28) that are necessary for reprogramming of a somatic cell and the nucleic acids encoding more than one kind of luminescent proteins that can emit the lights of different wavelength band regions; and this sample is the somatic cell that includes the gene group (construct) that can express a fused protein of the initializing factors and the luminescent genes.

In this specification, the nucleic acids have the same meaning as a gene, i.e., for example, DNA (deoxyribonucleic acid). The luminescent reporter protein is expressed by the luminescent gene; and then, the luminescent reporter protein thus expressed causes a luminescent substance to emit a light.

Also, the somatic cell may be, for example, a human peripheral blood mononuclear cell (PBMC), but not limited to this.

Preferably, the nucleic acids encoding the initializing factor and the nucleic acids encoding the luminescent protein are not introduced into a host's chromosome but into a somatic cell in the sustainably expressible form. For example, the nucleic acids encoding the initializing factor and the nucleic acids encoding the luminescent protein are introduced into the somatic cell in the form of an episomal vector. In this case, the episomal vector may be a commercially available product or a modified vector that is a commercially available episomal vector having the nucleic acids encoding the luminescent protein incorporated thereto. Illustrative examples of the commercially available episomal vector include pCXLE-hOct3/4-shp53 (Addgene), pCXLE-hSK (Addgene), and pCXLE-hUL (Addgene).

The nucleic acids encoding the initializing factors each may be incorporated into different vectors or into one vector. When the nucleic acids are incorporated into one vector, incorporation is preferably conducted, for example, by polycistronically connecting by way of a 2A sequence, an IRES sequence, or the like of a foot-and-mouth disease virus. In one example, one vector incorporated with one kind of initializing factor, or more than one kind of the vectors incorporated with the nucleic acids encoding two kinds of initializing factors by way of the 2A sequence are prepared, and then they are mixed; then, the resulting mixture including the nucleic acids encoding all the necessary initializing factors for induction of the iPS cell is introduced into a somatic cell. Here, the procedure of the gene introduction can be conducted by a heretofore known method.

In addition to the nucleic acids encoding the initializing factor and the nucleic acids encoding the luminescent protein, the nucleic acids encoding an additional factor that can enhance the reprogramming efficiency may be introduced into the somatic cell. Illustrative examples of the additional factor that can enhance the reprogramming efficiency include the factors that are known to enhance the reprogramming efficiency such as a mouse p53 and EBNA1 that are introduced with a dominant negative mutation. The additional factor to enhance the reprogramming efficiency is introduced into the somatic cell, for example, in the form of the episomal vector. In this case, commercially available episomal vectors, such as pCE-mp53DD (Addgene) and pCXB-EBNA1 (Addgene), may be used.

More than one kind of the initializing factors that are necessary for reprogramming of the somatic cell may be two or more transcription factors selected from the transcription factor group consisting of, for example, Oct4, Klf4, Sox2, L-myc, and LIN28, as described before. The number of the kinds of the initializing factors that are necessary for reprogramming of the somatic cell is, for example, 3 to 6. For example, the vector set, composed of the vector including the nucleic acids encoding Klf4 and the nucleic acids encoding Sox2, the vector including the nucleic acids encoding L-myc and the nucleic acids encoding LIN28, and the vector including the nucleic acids encoding Oct3/4, may be used as the initializing factors. In this embodiment, a plurality of combinations of the transcription factors selected from the group of the transcription factors may be used.

As for the nucleic acids encoding the luminescent protein, more than one kind of the nucleic acids, expressing respective combinations of the transcription factors, may be used. It is preferable to polycistronically connect with nucleic acids encoding the transcription factors, for example, by way of a 2A sequence or an IRES sequence of a foot-and-mouth disease virus. The location of the nucleic acids encoding the luminescent protein may be anywhere so far as both the transcription factor and the luminescent protein can be expressed; and the location thereof may be any in the upstream and the downstream of the nucleic acids encoding the transcription factor. In this embodiment, luciferases having different emitting colors (different wavelength band regions of the emitting light) may be used as the luminescent protein. Illustrative examples of the luciferase include: beetle's luciferases such as *P. pyralis*, click beetles, MA-Luci2, and SfRE1; marine luciferases such as renilla reniformi luciferase, sea firefly luciferase, aequorin, copepod luciferase, and oplophorus luciferase; and various luciferases such as bacterium luciferase and dinoflagellate luciferase. Specifically, illustrative examples of the luciferase include an Eluc luciferase that emits a green light, a CRB luciferase that emits a red light, and a renilla reniformi luciferase that emits a blue light. In particular, the luciferase originated from a firefly and the luciferase originated from a beetle such as a click beetle are ATP-demanding, so that a dead cell having lost a biological reaction does not emit a light; thus, these are preferable from the viewpoint that a living cell can be selectively observed without the cells inactivated by apoptosis or the like during the culture period.

Because the luminescent protein expresses with the transcription factor, the expression timing and expression amount of the gene encoding the luminescent protein can be deemed to correspond to those of the initializing factor. When the luciferase is used as the luminescent protein, a luciferin is added to emit a light. Illustrative examples of the luciferin include a firefly luciferin, a bacterium luciferin, a dinoflagellate luciferin, vargulin, and coelenterazine.

The sample 2 (somatic cell) changes to the iPS cell in such a way that after the culture period, the nucleic acids encoding the initializing factor and the nucleic acids encoding the luminescent protein are expressed to induce the reprogramming of the somatic cell. In this change, over a plurality of transplanting periods, part of the cell group after culturing is transplanted (a colony (cell group) after culturing in a prescribed culture vessel for a prescribed period is transplanted to a new culture vessel), so that the reprogramming is induced in stages. "Reprogramming" means the phenomenon that the differentiated cell is changed to a pluripotent stem cell, or that the differentiated cell is initialized.

A single somatic cell introduced with the genes grows to a cell group called a colony by culturing for a prescribed period. In general, the transplanting process that is repeated over the entire period of the reprogramming process is conducted by fractionating the cell group in a prescribed area including a barycentric position in each colony with a pipet or the like.

The number of the transplanting process necessary for preparation of the iPS cell is 5 to 10. When the number reaches this necessary number, it is deemed that the reprogramming process is over; then, the final pass/fail judgement is done by using a reagent to check the function as the iPS cell. The pass/fail judgement is done by the test to check the pluripotency in differentiation of the cell. Here, the test is conducted, for example, by a PCR method or an immunostaining method. Only the iPS cell having passed this final test can be used for the purpose of the studies of the regenerative medicine and so forth.

Specifically, illustrative examples of the quality assessment of the iPS cell include assessment of the reprogramming state and assessment of the differentiation potency.

Illustrative examples of the assessment of the reprogramming state include an analysis of an alkaline phosphatase activity, a karyotype analysis, and an expression analysis of an undifferentiated marker.

Because the alkaline phosphatase can exhibit high expression in the pluripotent stem cell, this is one of the markers in the undifferentiated state. The alkaline phosphatase activity may be analyzed by conducting an alkaline phosphatase stain in accordance with a heretofore known method. In this analysis, by the alkaline phosphatase staining, existence or non-existence of the alkaline phosphatase activity may be judged, or the alkaline phosphatase activity may be quantified. In the alkaline phosphatase stain, for example, after formalin fixation, a mixed substrate solution of 5-bromo-4-chloro-3-indolyl phosphate (BCIP) and nitroblue tetrazolium (NBT) is added to detect a reaction product due to the alkaline phosphatase activity.

The karyotype analysis is conducted, for example, by analyzing the changes in the number and structure of the chromosome with the G-band analysis.

The expression analysis of the undifferentiated marker is conducted by the RT-qPCR of an undifferentiated marker gene, or by the immunostaining of an undifferentiated marker protein. Illustrative examples of the undifferentiated marker include Nanog, Oct3/4, TRA1-60, and TRA1-81.

The assessment of the differentiation potency is conducted, for example, by the expression analysis of the tridermic differentiation markers after induction to the tridermic cells. The expression analysis of the differentiation marker is conducted by the RT-qPCR of the differentiated marker and the immunostaining of the differentiation marker protein. Illustrative examples of the differentiation marker include ectoderm markers (PAX6 and MAP2), mesoderm markers (α-SMA and Branchyury), and endoderm markers (SOX17 and AFP).

Figure 3:
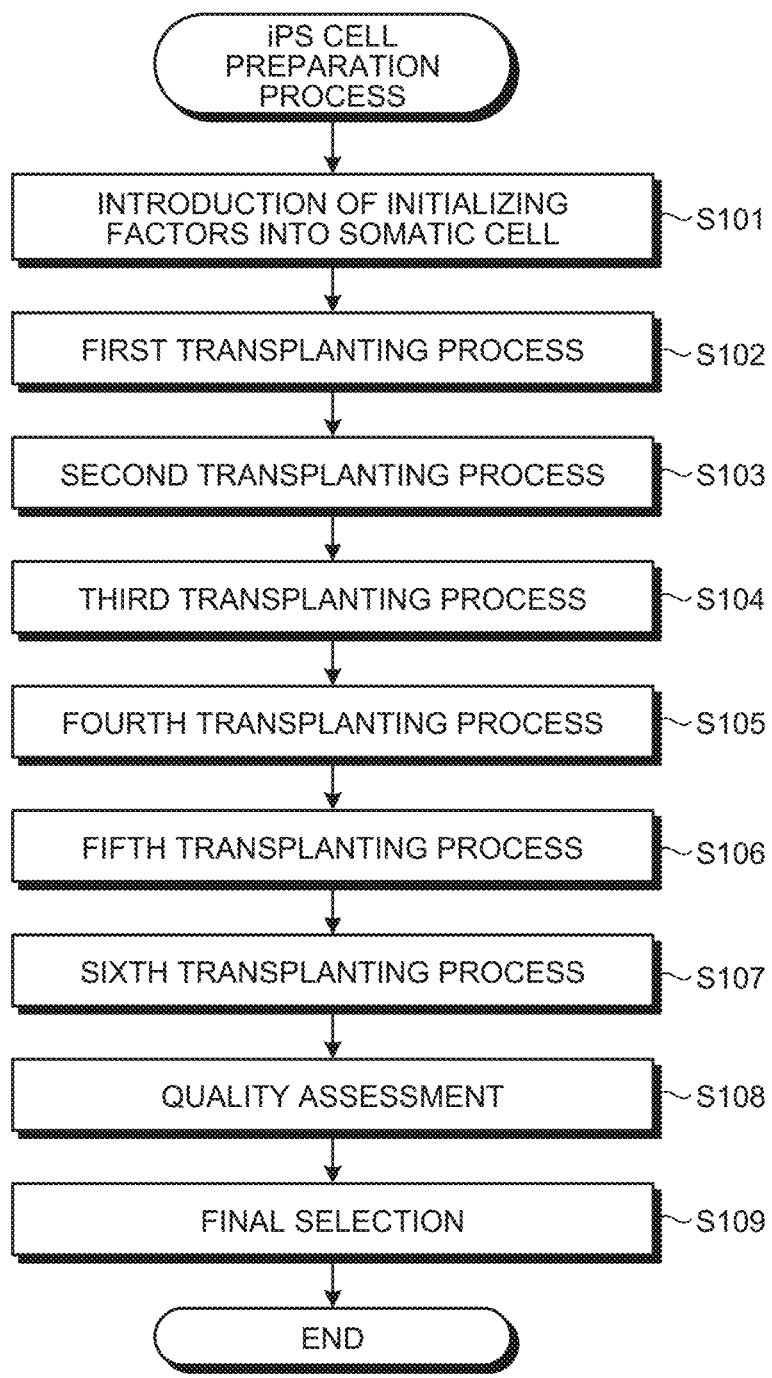
FIG. 3 is a drawing to explain the flow of the preparation process of the iPS cell in the first embodiment of the disclosure.

FIG. 3 is the drawing to explain the flow of the preparation process of the iPS cell in the first embodiment of the disclosure. In this first embodiment, explanation will be made as to the example where the number of the transplanting process is 6. Hereinafter, a period from a start of transplanting to a first transplanting and a period from after a transplanting to a next transplanting are also occasionally called "culture period".

At a step S101, the gene group (construct) that can express a fused protein of more than one kind of the initializing factors necessary for reprogramming and at least two luminescent genes are introduced into a somatic cell. In the first embodiment, one or a combination of two or more initializing factors, selected from Oct4, Klf4, Sox2, L-myc, and LIN28, is used.

The somatic cell introduced with the initializing factors at the step S101 is cultured, for example, for 20 to 25 days.

The step S101 corresponds to an initial stage of the reprogramming. The initial stage of the reprogramming includes a colony forming stage in which the cells are gathered thereby starting to rise up three-dimensionally.

At a step S102 after the step S101, the colony formed by culturing at the step S101 is transplanted to a different culture vessel (first transplanting process). In the first transplanting process, the transplanted colony is cultured for 7 to 10 days.

Then, similarly to the step S102, the process at which the colony formed by culturing is transplanted to a new culture vessel is repeated (step S103 to step S107). In the first embodiment, the transplanting process is repeated 6 times.

At a step S108 after the step S107, quality of the cells in the colony formed by the transplanted and cultured cell is assessed. The quality assessment is conducted, for example, by the PCR method or the immunostaining method, as described above.

At a step S109 after the step S108, on the basis of the quality assessment, the cell capable of becoming a good iPS cell is selected. The iPS cell prepared with this preparation process of the iPS cell is used for the purpose of the studies of the regenerative medicine and so forth.

Specifically, illustrative example of the vessel 3 include a Petri dish, a glass slide, and a microplate.

The imaging unit 5 composes an inverted microscope. The imaging unit 5 captures a luminescent image and a fluorescent image of the sample 2. The imaging unit 5 has an objective lens 51, a dichroic mirror 52, a light source 53, a charge coupled device (CCD) camera 54, a tube lens 55, and a shutter 56.

Specifically, the value of (numerical aperture/magnification)$^2$ of the objective lens 51 is 0.01 or more.

The dichroic mirror 52 transmits the light from the sample 2, and changes the advancing direction of the excitation light emitted from the light source 53 so as to irradiate the sample 2. In other words, the dichroic mirror 52 transmits the light in the wavelength band region detectable as the emitted light from the sample 2 and bends the light outside this wavelength band region.

At the time of capturing an image, the dichroic mirror 52 is changed as appropriate, for example, to the dichroic mirror matching to the transmitting wavelength (and reflecting wavelength) in accordance with the wavelength band region of the light to be observed. When only the emitting light is observed, the composition not having the dichroic mirror 52 may be used. When the composition not having the dichroic mirror 52 is used, a filter that transmits the light of the observing wavelength band region may be installed in front of the CCD camera 54.

The light source 53 is composed of a lamp such as a xenon lamp or a halogen lamp, a laser, or an LED (light emitting diode).

The CCD camera 54 captures an image of the sample 2, the light of which is projected, after going through the objective lens 51, the dichroic mirror 52, and the tube lens 55, on the light receiving surface of the CCD camera 54 to acquire the fluorescence image or a bright field image. The CCD camera 54 is communicably connected in a wired or wireless manner to the information communication terminal 10. When a plurality of the samples 2 are present in the image area, the CCD camera 54 may capture the fluorescent images and bright field images of the samples 2 included in the image area.

The tube lens 55 focuses the light entering to the tube lens 55 by way of the objective lens 51 and the dichroic mirror 52 to image the image including the sample 2.

The shutter 56 changes the wavelength band region of the light emitted from the light source 53. In other words, the shutter 56 changes the wavelength band region of the light irradiating the sample 2 by transmitting or shielding the light emitted from the light source 53.

Note that the imaging unit 5 may be arranged differently against the stage 4. The CCD camera may be exchanged with a complementary metal oxide semiconductor (CMOS) camera.

The information communication terminal 10 is composed of a personal computer. And the information communication terminal 10 is composed of a control unit 11, a memory unit 12, a clock generation unit 13, a communication interface unit 14, an input/output interface unit 15, an input unit 21, and an output unit 22. In the information communication terminal 10, these units are connected by a bus.

The memory unit 12 is a storage means. Specifically, this is composed of: a memory device such as random access memory (RAM) or read only memory (ROM); a fixed disk device such as a hard disk; a flexible disk; an optical disk; or the like. The memory unit 12 memorizes the data and the like acquired by processing in the respective units of the control unit 11.

In the clock generation unit 13, the time in the system is measured, and the clock to synchronize the actions of each part is generated.

The communication interface unit 14 mediates the communication among the information communication terminal 10, the stage 4, the light source 53, and the CCD camera 54. Namely, the communication interface unit 14 has the function to communicate the data with other terminals via a wired or wireless communication line.

The input/output interface unit 15 is connected to the input unit 21 and the output unit 22. In the output unit 22, a speaker and a printer, in addition to a monitor, may be used.

The input unit 21 is composed of inputting devices such as a keyboard, a mouse, a touch panel, and various switches, outputting the inputted signals, which are generated to these inputting devices by responding to the outside operation, to the input/output interface unit 15.

The control unit 11 carries out various processing in accordance with a program. The control unit 11 has an image capturing instruction unit 11a, an image acquisition unit 11b, a luminescence amount acquisition unit 11c, a judgement unit 11d, and a selection unit 11e. The control unit 11 is composed of a general processor such as CPU (central processing unit) and dedicated processors of various operation circuits to carry out specific functions such as ASIC (application specific integrated circuit).

Through the communication interface unit 14, the image capturing instruction unit 11a instructs the CCD camera 54 to capture a luminescent image and/or a bright field image.

Through the communication interface unit 14, the image acquisition unit 11b acquires the luminescent image and/or the bright field image, these having been captured by the CCD camera 54.

The luminescent image and bright field image acquired by the image acquisition unit 11b are interrelated with each other in their positions when the position of the stage 4, the position of the optical system including the objective lens 51, and the position of the optical system including the objective lens 51 are the same. Similarly, the positions of a plurality of the luminescent images with different wavelength band regions can also be interrelated with each other.

The luminescence amount acquisition unit 11c measures, on the basis of the luminescent image, the luminescence amount of the luminescent substance (luciferin in this case) emitted by the luminescent protein. Expression of the luminescent protein is caused by the luminescent gene, in which the luminescence amount is determined by the expression amount of the luminescent protein. In other words, this luminescence amount corresponds to the luminescent protein expressed by the luminescent gene, so that this can be regarded as the luminescence amount of the luminescent gene.

In the luminescent image, the luminescence amount acquisition unit 11c acquires the luminescence amount in a prescribed area including the barycentric position in each cell group (colony) in the sample 2. The luminescence amount acquisition unit 11c acquires the colony's outer boundary shape on the basis of the pixel number (brightness) to calculate the barycentric position of this shape. The colony's boundary shape is extracted as the contour thereof by binarizing the luminescent image (or the bright field image). The luminescence amount acquisition unit 11c calculates the luminescence amount on the basis of the pixel number in a prescribed area including the barycentric position thereby acquired. The luminescence amount is the photon number per unit area and unit time. The unit of the luminescence amount is, for example, photon/μm²/sec. Specifically, the luminescence amount (photon number) can be calculated by the following equation using the quantum efficiency of the CCD camera 54 at the wavelength of the luminescent protein, i.e., the detection target.

Photon Number=(output brightness−dark brightness)×conversion coefficient/(analog gain×EM gain×quantum efficiency/100)

Here, the values may be set to, for example, 5.8 for the conversion coefficient, 1.0 for the analog gain, 1,200 for the EM gain, and 90 for the quantum efficiency. The analog gain means the amplification factor of the analog luminance signal. The electron multiply (EM) gain means the electron multiplication factor in the light detecting surface of the CCD camera 54.

Note that even when the measurement instrument, capturing conditions, and optical filter characteristics are different from those disclosed in this specification, the luminescence amount (photon number) as the standard for the quality judgement may be calculated on the basis of the equation and the like as described above.

Because the cell group in a prescribed area including the barycentric position is pipetted at the time of transplanting, this is the necessary measurement area for selection of the iPS cell; and it is necessary to acquire the luminescence amount in the barycentric position or around the barycentric position. Here, the barycentric position is defined as a region having a prescribed area including the portion near the center of the colony and the portion where the cell is most densely populated. Specifically, the area near the barycentric position of the colony can be defined as the prescribed unit area (for example, a circle of a radius of within about 1 mm, or a rectangular) in the portion in the image where the cell density is the highest in the colony when the bright field image is observed.

To acquire the luminescence strength of each of the prescribed cultured colonies, first, the luminescent image is acquired in the observation field where the whole of the colony is included therein; then, on the basis of the luminescent image thereby acquired, the sum of the brightness values of the pixel included in the area corresponding to near the barycentric position is calculated. The luminescence amounts of the two luminescent genes in the cell group are acquired.

Hereinafter, the way how to calculate the barycentric position in the colony will be explained. The barycentric position is defined as the point that is set in the following coordinate in the bright field image acquired in the colony.

$$\left( \frac{\sum_{i=1}^{n}(xi \cdot Bi)}{\sum_{i=1}^{n} Bi}, \frac{\sum_{i=1}^{n}(yi \cdot Bi)}{\sum_{i=1}^{n} Bi} \right)$$

Here, n represents the number of the pixel that constitutes the bright field image.

In the Cartesian coordinates in which the x-coordinate and the y-coordinate are perpendicularly crossing to each other, xi represents the x-axis in the ith pixel, and yi represents the y-axis in the ith pixel in accordance with the pixel arrangement of the CCD camera 54. Bi represents the binarized value of the brightness in the ith pixel. Here, n and i both are an integer of 1 or more, and satisfy n≥i. The barycentric position in the colony may be set by using, for example, cellSens (manufactured by Olympus Corp.).

The judgement unit 11*d* judges whether the luminescence amount of each of the luminescent genes is more than a threshold by comparing the luminescence amount of each luminescent protein (hereinafter, this is also called luminescence amount of the luminescent gene) acquired by the luminescence amount acquisition unit 11*c* with the predetermined threshold relating to the luminescence amount of each of the luminescent genes. The threshold is determined by the photon number in light emission of each of the luminescent genes. Specifically, for example, on the basis of the photon number with which a good iPS cell could be selected in the past test in the combination of the initializing factors, the threshold is determined as follows. Note that the threshold corresponds to the relative luminescence amount (photon number) of the combined luminescent genes. When the following threshold is used, a good iPS cell can be selected highly efficiently.

Combination of the photon number of L-myc and LIN28 with the photon number of Sox2 and Klf4: no color separation.
(Selection Probability of the Good iPS Cell: 83%)
Threshold to the photon number of L-myc and LIN28: $1.72 \times 10^{-1}$ photons/μm²/sec.
Threshold to the photon number of Sox2 and Klf4: $3.59 \times 10^{-1}$ photons/μm²/sec.
(Selection Probability of the Good iPS Cell: 100%)
Threshold to the photon number of L-myc and LIN28: $2.30 \times 10^{-1}$ photons/μm²/sec.
Threshold to the photon number of Sox2 and Klf4: $3.59 \times 10^{-1}$ photons/μm²/sec.

Combination of the photon number of L-myc and LIN28 with the photon number of Sox2 and Klf4: color separation.
(Selection Probability of the Good iPS Cell: 83%)
Threshold to the photon number of L-myc and LIN28: $4.14 \times 10^{-1}$ photons/μm²/sec.
Threshold to the photon number of Sox2 and Klf4: $3.39 \times 10^{-2}$ photons/μm²/sec.
(Selection Probability of the Good iPS Cell: 100%)
Threshold to the photon number of L-myc and LIN28: $4.74 \times 10^{-1}$ photons/μm²/sec.
Threshold to the photon number of Sox2 and Klf4: $3.39 \times 10^{-2}$ photons/μm²/sec.

Combination of the photon number of L-myc and LIN28 with the photon number of Oct4: no color separation.
(Selection Probability of the Good iPS Cell: 75%)
Threshold to the photon number of L-myc and LIN28: $9.79 \times 10^{-1}$ photons/μm²/sec.
Threshold to the photon number of Oct4: $5.93 \times 10^{-1}$ photons/μm²/sec.
(Selection Probability of the Good iPS Cell: 100%)
Threshold to the photon number of L-myc and LIN28: 5.68 photons/μm²/sec.
Threshold to the photon number of Oct4: $7.25 \times 10^{-1}$ photons/μm²/sec.

Combination of the photon number of L-myc and LIN28 with the photon number of Oct4: color separation.
(Selection Probability of the Good iPS Cell: 71%)
Threshold to the photon number of L-myc and LIN28: 2.93 photons/μm²/sec.
Threshold to the photon number of Oct4: $1.92 \times 10^{-1}$ photons/μm²/sec.

(Selection Probability of the Good iPS Cell: 100%)
Threshold to the photon number of L-myc and LIN28: 2.93 photons/$\mu m^2$/sec.
Threshold to the photon number of Oct4: $3.28\times10^{-1}$ photons/$\mu m^2$/sec.

Here, in the case of "color separation", the acquired signal value is corrected to remove the cross talk on the basis of the transmittance of the optical filter in the dichroic mirror 52 and the like. On the other hand, in the case of "no color separation", the correction to remove the cross talk is not conducted.

On the basis of the judgement result of the judgement unit 11*d*, the selection unit 11*e* selects the colony including the cell capable of becoming the good iPS cell. Specifically, when the luminescence amount of each of the luminescent genes is more than the respective threshold thereof, on the basis of the judgement results of the judgement unit 11*d*, the selection unit 11*e* classifies the selected cells in decreasing order of the selection probability to the good iPS cell; then, this classification results are displayed in the output unit 22. By so doing, the cells capable of becoming the good iPS cell can be selected as many as possible in descendent order of quality.

Figure 4:
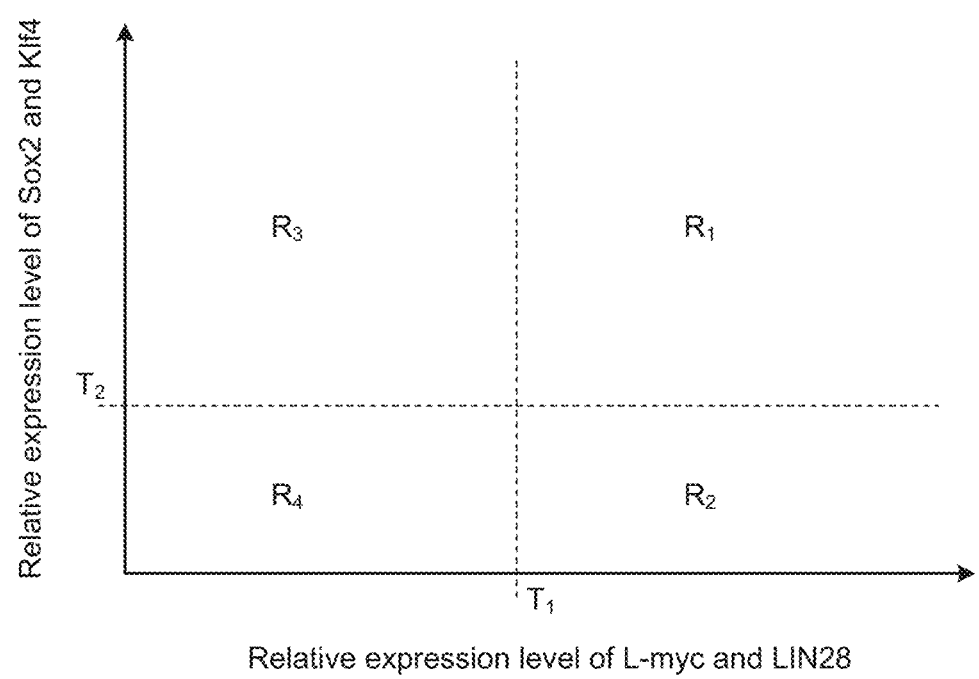
FIG. 4 is a drawing to explain the flow of the selection process of a suitable cell as the iPS cell in the first embodiment of the disclosure.

FIG. 4 is the drawing to explain the selection process to select a good cell as the iPS cell in the first embodiment of the disclosure. FIG. 4 illustrates the case in which the relative luminescence amount in the combination of L-myc and LIN28 and the relative luminescence amount in the combination of Sox2 and Klf4 are acquired, whereby the cells are selected by regarding these luminescence amounts as the expression amounts of these initializing factors. For example, when the threshold to the luminescence amount of L-myc and LIN28 is set to $T_1$ and the threshold to the luminescence amount of Sox2 and Klf4 is set to $T_2$, the cell that is selected as the cell capable of becoming the good iPS cell is distributed in the area $R_1$ where the luminescence amounts each are equal to or more than the thresholds $T_1$ and $T_2$. On the other hand, when the cell is distributed in the areas $R_2$ to $R_4$ where each of the luminescence amounts is less than at least one of the thresholds $T_1$ and $T_2$, this is not selected as the cell capable of becoming the good iPS cell.

Also, the control unit 11 produces an image by superimposing at least two images of a bright field image and one or a plurality of luminescent images with each other, the images being captured at the same point of time; then, the control unit directs the output unit 22 to display these images.

The input unit 21 is composed of inputting devices such as a keyboard, a mouse, a touch panel, and various switches, and outputs the inputted signals, which are generated by responding to outside operations to these inputting devices, to the control unit 11.

The output unit 22 is composed of displaying devices such as an LCD (liquid crystal display) or an EL (electroluminescence) display, and a printer; this unit is operated under the control of the control unit 11.

Figure 5:
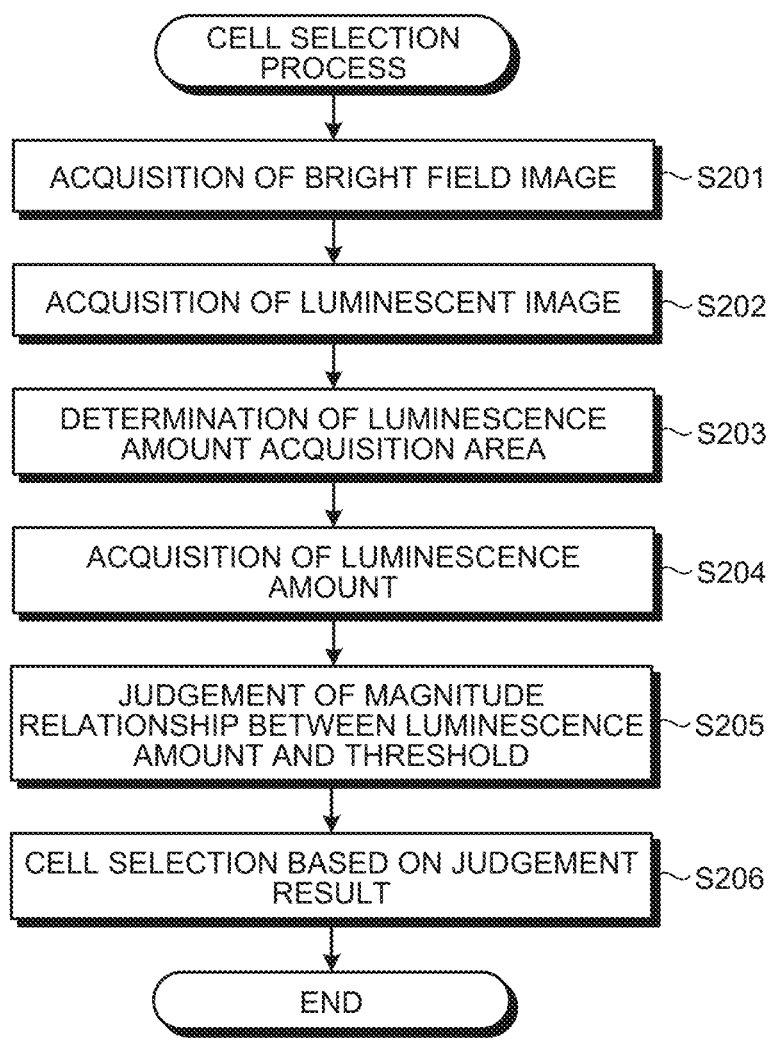
FIG. 5 is a drawing to explain the flow of the selection process of the iPS cell in the first embodiment of the disclosure.

One example of the processing that is conducted in the selection system 1 with the composition described above will be explained with referring to FIG. 5. FIG. 5 is the drawing illustrating the flow of the selection process of the iPS cell in the first embodiment of the disclosure.

In a step S201, the image capturing instruction unit 11*a* instructs the CCD camera 54 to capture the bright field image. The image acquisition unit 11*b* acquires the bright field image that was captured by the CCD camera 54.

At a step S202 after the step S201, the image capturing instruction unit 11*a* instructs the CCD camera 54 to capture the luminescent image. The image acquisition unit 11*b* acquires the luminescent image that was captured by the CCD camera 54. At this time, the lights in the wavelength band region that excite the luminescent genes having been introduced into the sample 2 are individually emitted (excitation lights).

The control unit 11 directs the memory unit 12 to memorize the bright field image and the luminescent image of each of the luminescent genes acquired at the step S201 and the step S202. For the sake of control, the images that are memorized here are processed as the images that were captured at the same point of time. For example, the acquiring time of the image is set at the starting time to acquire the bright field image, or between the starting time to acquire the bright field image and the ending time to acquire the luminescent image.

The exposure period at the capturing process can be changed as appropriate depending on the sensitivity of the imaging system (for example, image pickup element), optical characteristics of the imaging optical system, kinds of biological samples, kinds of luminescent genes, kinds of fluorescent reagents, culture conditions (temperature, ingredients in the culture medium, culture period, and the like), and the like.

In general, the exposure period in the image pickup element at the time of acquiring the luminescent image is significantly longer than that of the bright field image and the fluorescent image (for example, 5 to 60 minutes, although this is different depending on the growing stage of the biological sample and the size of the biological sample).

Capturing of the luminescent image may be done intermittently by dividing the exposure period with regard to the luminescent image into a plurality of times.

It is preferable to control the timing and the like of capturing so as to maintain the highly precise cell assessment even when the cell moves during the necessary exposure period to acquire the luminescent image.

At a step S203, in the luminescent image thereby captured, the luminescence amount acquisition unit 11*c* acquires the colony's barycentric position in the sample 2, and determines a certain area including the barycentric position as the area where the luminescence amount is acquired.

At a step S204 after the step S203, from the pixel value in the area thus determined, the luminescence amount acquisition unit 11*c* acquires the luminescence amount of each of the luminescent genes in the colony.

At a step S205 after the step S204, the judgement unit 11*d* judges whether the luminescence amount of each of the luminescent genes is more than the threshold thereof. The judgement unit 11*d* compares the luminescence amount acquired at the step S204 with the predetermined threshold in each of the luminescent genes; then, the judgement unit judges the magnitude relationship of them.

Then, on the basis of the judgement result by the judgement unit 11*d*, the selection unit 11*e* selects the colony that includes the cell capable of becoming the good iPS cell (step S206). Specifically, when the luminescence amount of each of the luminescent genes is more than the threshold thereof (for example, when these are distributed in the area $R_1$ in FIG. 3), the selection unit 11*e* selects this cell as the colony that includes the cell capable of becoming the good iPS cell.

The selection process described above is conducted before the first transplanting process or at the later stage in the first transplanting period. By selecting the cell at the early stage of culturing, only the cell capable of becoming the good iPS cell can be inherited. As a result, ineffectual culturing due to transplanting of the cells incapable of becoming the good iPS cell can be avoided.

In the first embodiment explained above, the selection is conducted by combining the comparison result between the luminescence amount of each of the luminescent genes and the threshold thereof, so that only by the expression amount, the cell group (colony) capable of becoming a high-quality iPS cell with high probability and the cell group that is assessed to have a low quality or be incapable of becoming the iPS cell with high probability can be selected. In the first embodiment, from all the cell groups, the high-quality cell can be selected and a low-quality cell can be removed with objective judgement. According to the first embodiment, the good iPS cell can be selected highly efficiently and precisely.

According to the first embodiment, the cell near the barycentric position in the cell group is selected, so that the expression amount sufficient for selection can be acquired without being affected by the contour of the cell group or the fluctuation of the cell density in the position of the cell group.

According to the first embodiment, the threshold is set to each initializing factor, so that the good cell group (colony) can be easily selected.

According to the first embodiment, the luminescent protein is used for observation and selection, so that not only the processing can be carried out with minimal invasion to the cell but also the result is highly quantitative. In this embodiment, when the fluorescence is observed by using a fluorescent protein, an excitation light needs to be emitted. The excitation light is known to have phototoxicity to the cell. For example, the excitation light is involved in generation of an active oxygen species, so that the active oxygen species can be an oxidative damaging factor to DNA. The light with the wavelength to excite a fluorescent protein typically represented by GFP can cause membrane blebs and abnormal cell division. In addition, the expression of the fluorescent protein itself can cause the cell induction. On the other hand, observation of the emitted light without using the excitation light can be done with a low damage to the cell even when the observation is conducted for a long period of time. Besides, expression of the luminescent protein is harmless to the cell.

When quantification is done with the fluorescent protein, autofluorescence is frequently observed at the time of detecting the fluorescent protein. On the other hand, when quantification is done with the luminescent protein, no background due to autofluorescence is observed; and this is excellent in quantitativity.

According to the first embodiment, the luminescent protein is used for observation and selection; therefore, this is excellent in observation and selection at an early stage. Maturing of the fluorescent protein needs 3 hours at the shortest, and about 20 hours at the longest. In particular, a red fluorescence matures via a green fluorescence in the maturing process; therefore, it is difficult to distinguish from the green fluorescence in the maturing process. On the other hand, the luminescent protein such as luciferase matures instantly upon induction of the expression. Therefore, the luminescent protein is suitable for observation at the early stage of the reprogramming.

Also, according to the first embodiment, because the good iPS cell can be selected at the early stage, the preparation load can be significantly reduced. In addition, in the first embodiment, because there is no selection conducted after the early stage, the preparation cost of the iPS cell can be lowered.

The first embodiment may be configured to arrange a diaphragm and a phase plate so that a phase difference observation image may be acquired.

In the first embodiment, combination of the initializing factors for the judgement standard is arbitrary. In fact, the inventors of the disclosure exhaustively tested the combinations of the initializing factors other than the combinations described in the first embodiment; then, the prescribed threshold was able to be calculated similarly. On the other hand, from the test results, it was found that the assessment with the combination of L-myc and LIN28 and the combination of Sox2 and Klf4 as described in the first embodiment is more preferable than the assessment with other combinations, because the fluctuation in acquiring the good iPS cell was less and the colony of the iPS cell could be selected more efficiently.

In the first embodiment, the explanation was made as to the example in which the luminescence amount is measured in the first period (before the first transplant) of the culture period (namely, at the same points of time soon after the start of culturing). On the other hand, in the bioluminescence that is used in the first embodiment, the light is emitted continuously and quantitatively. Accordingly, in the same culture period, even when the luminescence amount is measured at the different points of time (for example, at a specific time and a time that is followed thereafter, i.e., the time that is different from the specific time), it was found that the good iPS cell can be judged when the amount is more than the threshold found by the method of the first embodiment.

In the light emission of the cell, by the action of the episomal vector, there is a tendency that the luminescence amount as the measured value decreases on the whole as the culturing progresses, and thereafter, the luminescence amount is stable at a comparatively low level, which is then followed by gradual vanishing. Here, the decay rate of the luminescence amount is identical regardless of the kinds of the transcription factor; and it was confirmed that in the luminescence amount at the same point of time before and after the decay, too, the ratio of the luminescence amount of the transcription factors at the same point of time does not change before and after the decay caused by the action of the episomal vector. Accordingly, by multiplying the reciprocal number of the decay rate of the luminescence amount that is reduced with progress of the culturing, the photon number compensated by the reduced luminescence amount caused by the temporal decay (compensated luminescence amount) can be obtained, so that the comparison can be made by using this compensated luminescence amount and the threshold described in the first embodiment as it is. With the compensation described above, not only in the first period but also after the transplanting process, the yield may be raised by continuing, as far as the luminescence can be detected, to monitor whether the iPS cell is suitable.

Namely, the selection process according to the first embodiment can be conducted by using the luminescence amount based on the images acquired at different points of time in the same culture period or at the points of time in different culture periods. In this case, a luminescence amount obtained at a specific point of time before a first transplanting to a culture vessel and a luminescence amount obtained at a subsequent point of time that is different from the before-mentioned specific point of time are acquired; and then, when the selection process is conducted by using the luminescence amount acquired at the subsequent point of time, the selection is conducted by using the compensated luminescence amount that is the subsequent luminescence amount compensated with the reduced amount from the first luminescence amount (compensated luminescence amount).

Second Embodiment

Figure 6:
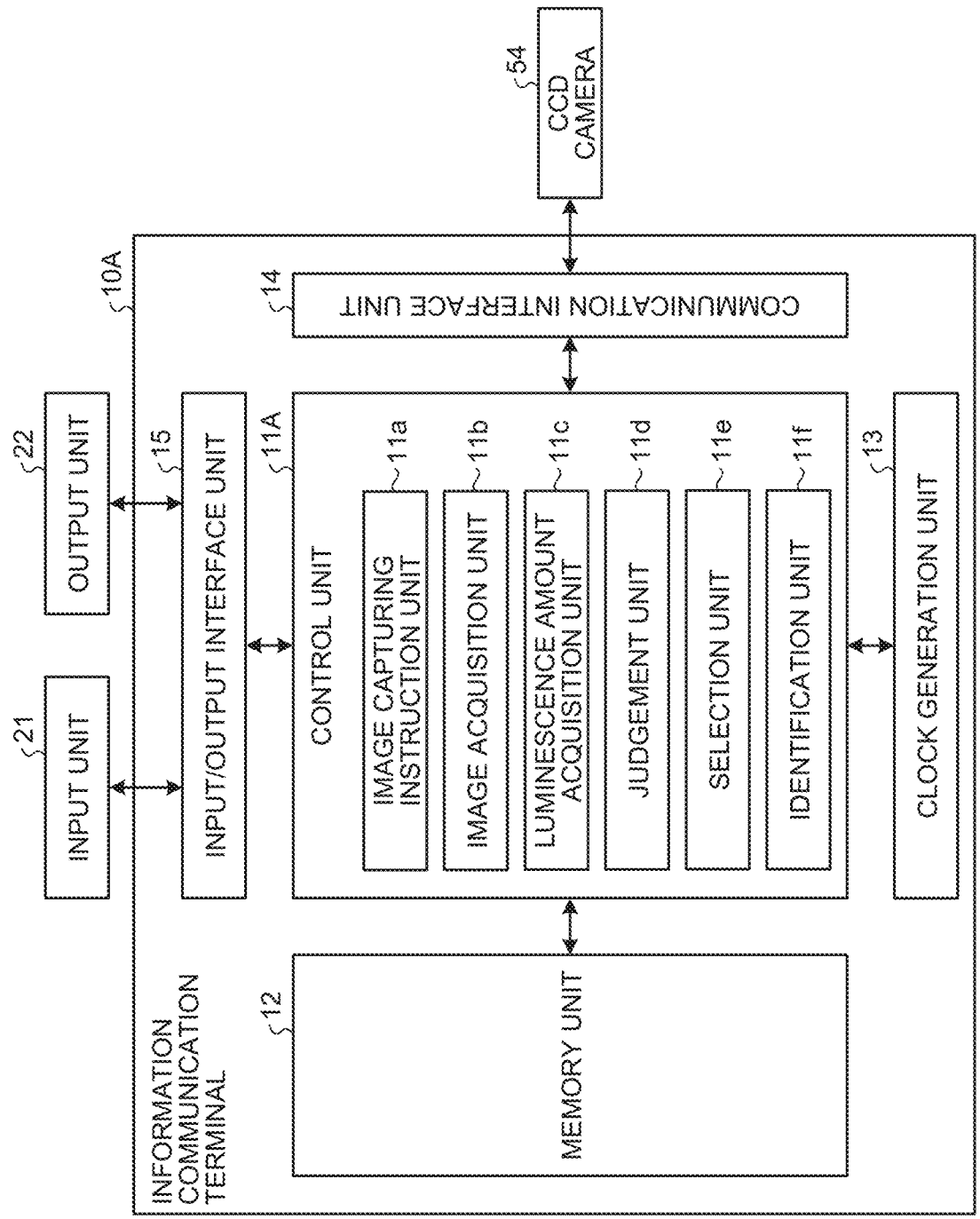
FIG. 6 is a block diagram illustrating the functional composition of the information communication terminal in the selection system of the iPS cell according to a second embodiment of the disclosure.

Next, a second embodiment of the disclosure will be explained. FIG. 6 is the block diagram illustrating the functional composition of the information communication terminal in the selection system of the iPS cell according to the second embodiment of the disclosure. The selection system according to the second embodiment is provided with the sample 2, the vessel 3 that accommodates the sample 2, the stage 4 on which the vessel 3 is disposed, the imaging unit 5, and an information communication terminal 10A. The selection system according to the second embodiment has the same composition as the selection system 1 except that the information communication terminal 10 is changed to the information communication terminal 10A. Hereinafter, explanation will be made as to the information communication terminal 10A whose composition is different from that of the first embodiment.

The information communication terminal 10A is composed of a personal computer. And the information communication terminal 10A is composed of a control unit 11A, the memory unit 12, the clock generation unit 13, the communication interface unit 14, the input/output interface unit 15, the input unit 21, and the output unit 22. In the information communication terminal 10A, these units are connected by a bus.

The control unit 11A carries out various processing in accordance with a program. The control unit 11A has the image capturing instruction unit 11a, the image acquisition unit 11b, the luminescence amount acquisition unit 11c, the judgement unit 11d, the selection unit 11e, and an identification unit 11f. The control unit 11A is composed of a general processor such as CPU (central processing unit) and dedicated processors of various operation circuits to carry out specific functions such as ASIC (application specific integrated circuit). The image capturing instruction unit 11a, the image acquisition unit 11b, the luminescence amount acquisition unit 11c, the judgement unit 11d, and the selection unit 11e have the same compositions and functions as those of the first embodiment. Hereinafter, the composition and processing of the identification unit 11f will be explained.

The identification unit 11f compares the images that are different in the capturing time, identifies the cells (or colonies) appearing in each image, and interrelates the cells (or colonies) appearing in the images. First, from the luminescence profile of each image, the identification unit 11f respectively specifies the notable areas where the cell can exist (hereinafter, these are also called the notable areas). The luminescence profile obtained at this time is prepared by using, for example, the luminescence strength, the luminescence strength distribution, or a combination of them.

The identification unit 11f calculates the characteristic quantity of the specified notable area of each image by using the identified notable area and the luminescence profile. The identification unit 11f compares the characteristic quantities among the images and then interrelates the cells (or colonies) included in the notable area. The characteristic quantity is, for example, the strength ratio of the luminescence strengths in the notable area. The identification unit 11f may conduct the identification process by using the luminescence amount of the colony that was used by the selection unit 11e.

In the second embodiment, the cell is successively tracked by interrelating the notable areas in the images that are acquired at different times.

Figure 7:
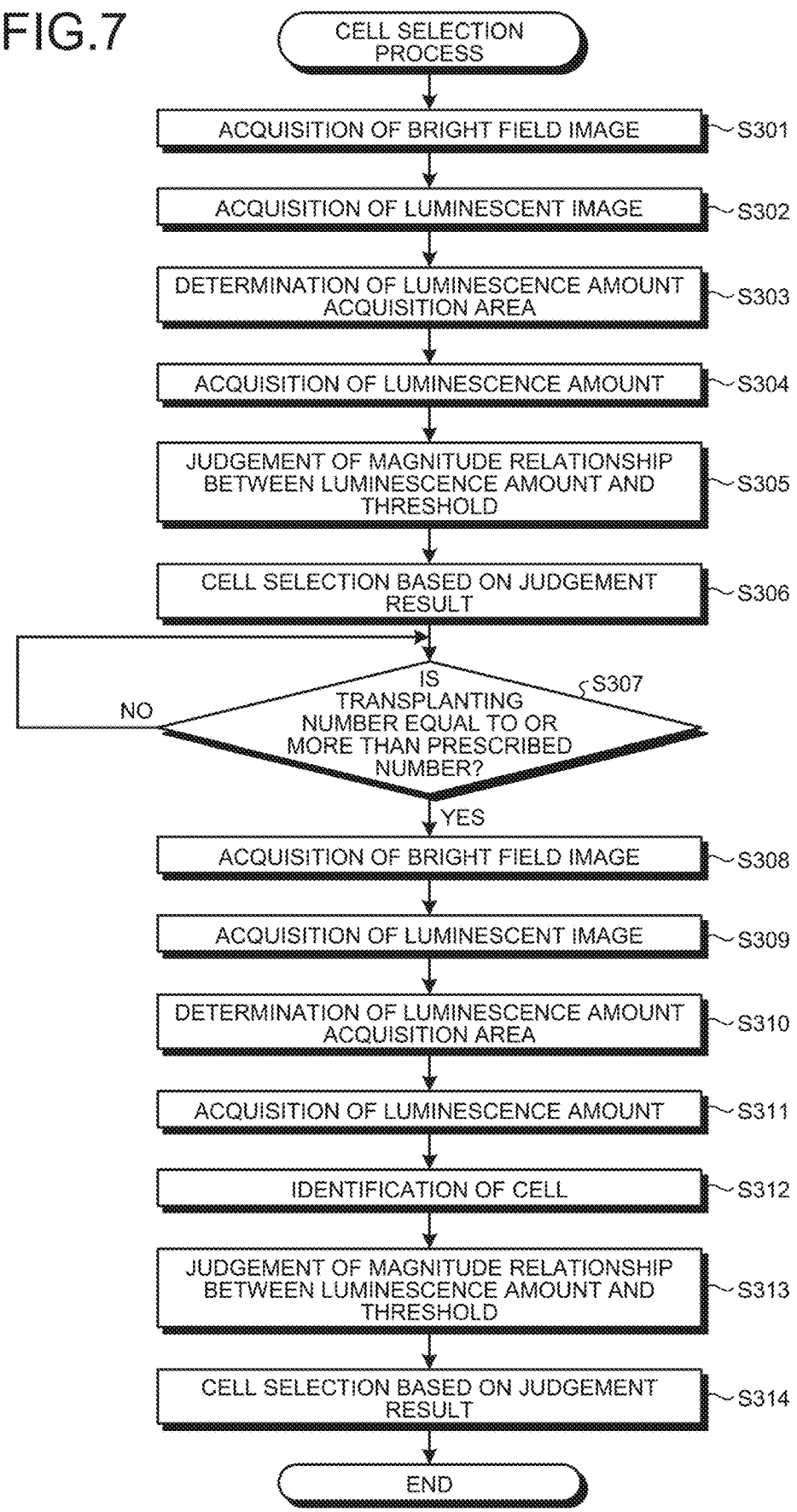
FIG. 7 is a drawing illustrating the flow of the selection process of the iPS cell in the second embodiment of the disclosure.

In the composition described above, one example of the process that is conducted in the selection system 1 will be explained with referring to FIG. 7. FIG. 7 is the drawing illustrating the flow of the selection process of the iPS cell in the second embodiment of the disclosure.

At a step S301, the image capturing instruction unit 11a instructs the CCD camera 54 to capture the bright field image, similarly to the step S201. The image acquisition unit 11b acquires the bright field image that was captured by the CCD camera 54.

At a step S302 after the step S301, the image capturing instruction unit 11a instructs the CCD camera 54 to capture the luminescent image, similarly to the step S202 described before. The image acquisition unit 11b acquires the luminescent image that was captured by the CCD camera 54.

The control unit 11A directs the memory unit 12 to memorize the bright field image and the luminescent image of each of the luminescent genes acquired at the step S301 and the step S302. For the sake of control, the images that are memorized here are regarded as an image acquired at the same point of time.

At a step S303, in the luminescent image thereby captured, the luminescence amount acquisition unit 11c determines the colony's barycentric position in the sample 2, and then determines a certain area including the barycentric position as the area where the luminescence amount is acquired.

At a step S304 after the step S303, from the pixel value in the area thereby determined, the luminescence amount acquisition unit 11c acquires the luminescence amount of each of the luminescent genes in the colony.

At a step S305 after the step S304, the judgement unit 11d judges whether the luminescence amount of each of the luminescent genes is more than the threshold thereof. The judgement unit 11d compares the luminescence amount acquired at the step S304 with the predetermined threshold in each luminescent gene, and then judges the magnitude relationship of them.

Then, on the basis of the judgement result by the judgement unit 11d, the selection unit 11e selects the colony that includes the cell capable of becoming the good iPS cell (step S306). On the basis of the judgement result by the judgement unit 11d, the selection unit 11e selects the colony that includes the cell capable of becoming the good iPS cell. Specifically, when the luminescence amount of each of the luminescent genes is more than the threshold thereof (for example, when this is distributed in the area $R_1$ in FIG. 3), the selection unit 11e selects this cell as the colony that includes the cell capable of becoming the good iPS cell.

After the step S306, the first transplanting process is carried out. The transplanting process is carried out, for example, as to the colony that was selected at the step S306. Therefore, in the transplanting process, only the selected colony that is capable of becoming the good iPS cell is transplanted. After the transplanting process, the control unit 11A confirms the number of the transplanting process (step S307). The control unit 11A confirms, for example, on the basis of the inputted signal received by the input unit 21, the number of the transplanting process. The control unit 11A judges whether the number of the transplanting process is equal to or more than the predetermined number. When the number of the transplanting process is less than the predetermined number (No at S307), the control unit 11A repeats the judgement about the number of the transplanting process. On the other hand, when the control unit 11A judges that the number of the transplanting process is equal to or more than the predetermined number (Yes at S307), the process moves to a step S308.

The number of the transplanting process that is predetermined here is set such that this number may be less than the transplanting number in preparation of the iPS cell and suitable for tracking the cultured cell.

The period during which the luminescent image can be acquired is limited to the period during which the nucleic acids encoding the initializing factor and the nucleic acids encoding the luminescent protein can be kept in the somatic cell. For example, when the nucleic acids encoding the initializing factor and the nucleic acids encoding the luminescent protein are introduced into the somatic cell in the form of the episomal vector, the luminescence can be captured from immediately after start of the reprogramming induction, namely after the episomal vector is introduced into the somatic cell, until the episomal vector is discharged to outside of the somatic cell.

At the step S308, the image capturing instruction unit 11a instructs the CCD camera 54 to capture the bright field image, similarly to the step S301 described before. The image acquisition unit 11b acquires the bright field image that was captured by the CCD camera 54.

At a step S309 after the step S308, the image capturing instruction unit 11a instructs the CCD camera 54 to image the luminescent image, similarly to the step S302 described before. The image acquisition unit 11b acquires the luminescent image that was captured by the CCD camera 54.

The control unit 11A directs the memory unit 12 to memorize the bright field image and the luminescent image of each of the luminescent genes acquired at the step S308 and the step S309.

At a step S310, in the luminescent image thereby imaged, the luminescence amount acquisition unit 11c determines the colony's barycentric position in the sample 2, and then determines a certain area including the barycentric position as the area where the luminescence amount is acquired.

At a step S311 after the step S310, from the pixel value in the area thereby determined, the luminescence amount acquisition unit 11c acquires the luminescence amount of each of the luminescent genes in the colony.

In a step S312 after the step S311, the identification unit 11f compares the bright field images that are acquired at the step S301 and the step S308, identifies the cells (or colonies) appearing in each image, and interrelates both of these.

At a step S313 after the step S312, the judgement unit 11d judges whether the luminescence amount of each of the luminescent genes is more than the threshold thereof. The judgement unit 11d compares the luminescence amount acquired at the step S304 with the predetermined threshold in every luminescent gene, and then judges the magnitude relationship of them.

Then, on the basis of the judgement result by the judgement unit 11d, the selection unit 11e selects the colony that includes the cell capable of becoming the good iPS cell (step S314).

At the step S314, because the selection is conducted only to the cell that was selected at the step S306, basically all the cells are selected as the cell that is capable of becoming the good iPS cell. At this time, due to external factors and the like, there is a case that some are judged as the cells that are incapable of becoming the good iPS cell; and it can also be said that the step S314 is to select the cell that was dropped out from the cell capable of becoming the good iPS cell during the course of transplanting.

In the second embodiment explained above, the selection is conducted by a simple method in which the comparison result between the luminescence amount of each of the luminescent genes and the threshold thereof are merely combined, so that only by the expression amount, the cell group (colony) capable of becoming a high-quality iPS cell with high probability and the cell group that is assessed to be a low-quality or incapable of becoming the iPS cell with high probability can be selected. In the second embodiment, from all the cell groups, the high-quality cell can be selected and the low-quality cell can be removed with the objective judgement. According to the second embodiment, the good iPS cell can be selected highly efficiently and precisely.

In the second embodiment, because the selection process is conducted again after the predetermined transplanting process, the cell that has been changed to being unacceptable during the course of transplanting is removed from the transplanting object. According to the second embodiment, the good iPS cell can be selected with a further high precision. In addition, wrong selection of the cell can be avoided, so that the quality of the prepared iPS cell can be enhanced.

In the above description, the embodiments to carry out the disclosure have been explained, but the disclosure shall not be limited only by the embodiments described above. The disclosure can include various embodiments and so forth that are not described here.

EXAMPLES

Hereinafter, the disclosure will be further explained in detail by Examples. However, the disclosure shall not be interpreted restrictively by Examples. In Examples, Oct3/4, Sox2, Klf4, L-myc, and LIN28 were used as the reprogramming induction factors. Among these induction factors, to each of Oct3/4, Sox2, and Klf4 was connected luciferase as the luminescent reporter protein to assess the expression state of each induction factor from the luminescent image thereof.

1-1. Preparation of Vectors

For induction of reprogramming, following three episomal vectors were prepared.
(1) Vector expressing L-Myc and LIN28 (pCE-hUL-Oki_mut1);
(2) Vector expressing Sox2, Klf4, and Oki_mut1 luciferase (pCXLE-hSK-Oki_mut1); and
(3) Vector expressing Oct3/4 and SfRE1 luciferase (pCXLE-hOct3/4-SfRE1)

These three kinds of the vectors are called "modified vector set". The transcription factors were selected on the basis of Okita K, et al., Nat. Methods 2011 May; 8(5): 409-412, "A more efficient method to generate integration-free human iPS cells".

Figure 8:
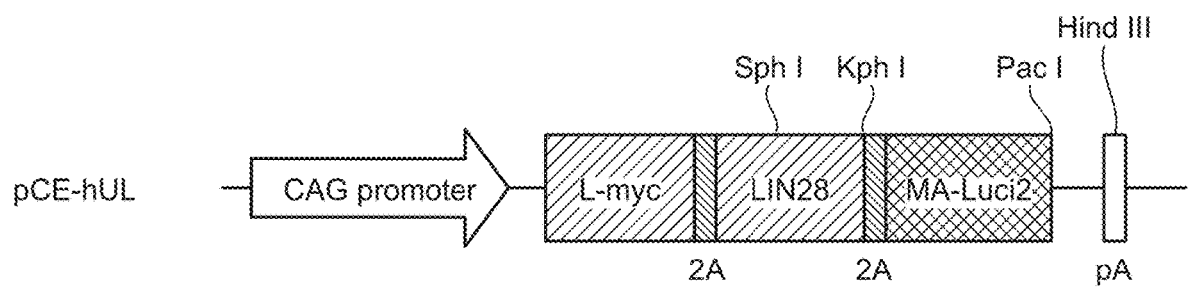
FIG. 8 is a drawing illustrating the composition of the pCE-hUL vector in Example.
Figure 9:
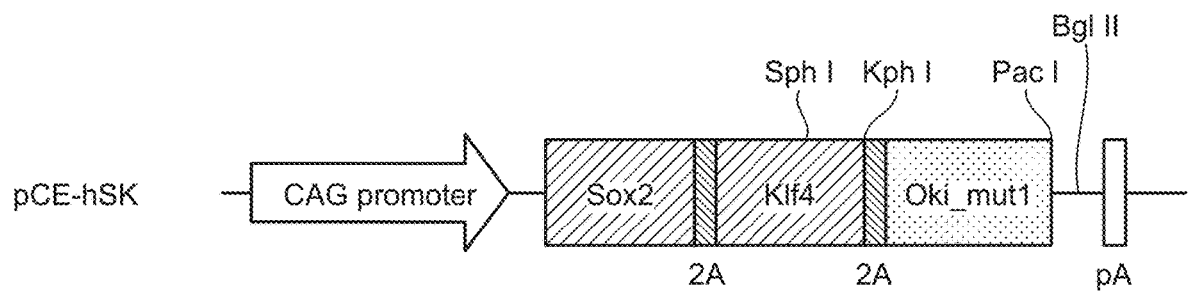
FIG. 9 is a drawing illustrating the composition of the pCE-hSK vector in Example.
Figure 10:
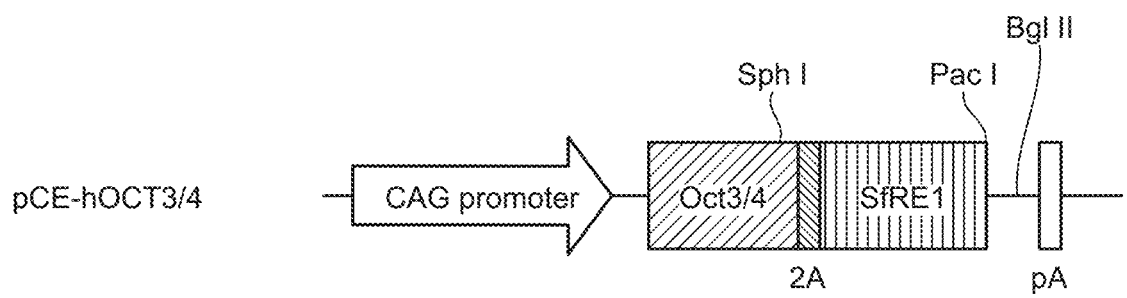
FIG. 10 is a drawing illustrating the composition of the pCXLE-hOct3/4-SfRE1 vector in Example.

Below, details of the vectors of (1) to (3) are described. FIG. 8 is the drawing illustrating the composition of the pCE-hUL vector in Example. FIG. 9 is the drawing illustrating the composition of the pCE-hSK vector in Example. FIG. 10 is the drawing illustrating the composition of the pCXLE-hOct3/4-SfRE1 vector in Example.

(1) pCXLE-hUL

The vector pCXLE-hUL was purchased from Addgene (see FIG. 8).

(2) pCXLE-hSK-Oki_mut1

The vector pCXLE-hSK-Oki_mut1 was prepared such that the Oki_mut1 luciferase may express as the luminescent reporter protein together with Sox2 and Klf4.

Specifically, the expression vector was prepared by digesting pCXLE-hSK (Addgene) with Spn I and Bgl II followed by incorporating the Oki_mut1 Luciferase (sequence No. 1) in the downstream of Kfl4 via the 2A sequence (see FIG. 9). With regard to the Kpn I site illustrated in FIG. 9, this was inserted after the sequence having the stop codon including the Kpn I site removed from inside of Klf4 was artificially synthesized.

(3) pCXLE-hOct3/4-shp53-SfRE1

The vector pCXLE-hOct3/4-shp53-SfRE1 was prepared such that the pCXLE1 luciferase may express as the luminescent reporter protein together with Oct3/4.

Specifically, the expression vector was prepared by digesting pCXLE-hOct3/4-shp53 (Addgene) with Kpn I and Bgl II followed by incorporating the SfRE1 Luciferase (sequence No. 2) in the downstream of hOct3/4 via the 2A sequence (see FIG. 10).

Below, the base sequences of the Oki_mut1 Luciferase and of the SfRE1 Luciferase are described.

OKi_mut1 Luciferase
(Sequence No. 1)
ATGGAAGATGACCACAAGAACATCGTGCACGGCCCTGCCCCATTCTACCC

CCTGGAAGAGGGAACAGCCGGCGAGCAGCTGCACCGGGCCATGAAGAGAT

ATGCCCAGGTGCCCGGCACAATCGCCTTCACCGATGCCCACGTGGAAGTG

AACATCACCTACAGCGAGTACTTCGAGATGGCCTGCCGGCTGGCCGAGAC

AATGAAGCGCTATGGCCTGGGCCTGCAGCACCACATTGCCGTGTGCAGCG

AGAACAGCCTGCAGTTCTTCATGCCCGTGTGTGGCGCCCTGTTCATCGGA

GTGGGAGTGGCCCCCACCAACGACATCTACAACGAGAGAGAGCTGTACAA

CAGCCTGAGCATCAGCCAGCCCACCATCGTGTTCTGCAGCAAGCGGGCCC

TGCAGAAAATCCTGGGCGTGCAGAAAAAGCTGCCCGTGATCGAGAAGATC

GTGATCCTGGACAGCCGCGAGGACTACATGGGCAAGCAGAGCATGTACAG

CTTCATCGAGAGCCATCTGCCCGCTGGCTTCAACGAGTACGACTACGTGC

CCGACACCTTCGACAGAGAGACAGCCACCGCCCTGATCATGAACAGCAGC

GGCTCTACCGGCCTGCCCAAGGGCGTGGAACTGACCCACAAGAATGTGTG

CGTGCGGTTCAGCCACTGCCGGGACCCTGTGTTCGGCAACCAGATCATCC

CCGACACCGCTATCCTGACCGTGATCCCCTTCCACCACGGCTTCGGCATG

TTCACCACCCTGGGCTACCTGACCTGCGGCTTCCGGATCGTGCTGATGTA

CAGATTCGAGGAAGAACTGTTCCTGCGGAGCCTGCAGGACTACAAGATCC

AGAGCGCCCTGCTGGTGCCTACCCTGTTCAGCTTCTTCGCCAAGAGCACC

CTGGTGGATAAGTACGACCTGAGCAACCTGCACGAGATCGCCTCTGGCGG

AGCCCCCCTGGCTAAAGAAGTGGGAGAGGCCGTGGCCAAGCGGTTCAAGC

TGCCTGGCATCAGACAGGGCTACGGCCTGACCGAGACAACCTCTGCCGTG

ATCATCACCCCCAGGGGCGACGATAAGCCTGGCGCCTGTGGAAAGGTGGC

CCCATTTTTCAGCGCCAAGATTGTGGACCTGGACACCAGCAAGACACTGG

GCGTGAACCAGAGGGGCGAGCTGTGTCTGAAGGGCCCCATGATTATGAAG

GGCTACGTGAACAACCCCGAGGCCACCAATGCCCTGATCGACAAGGATGG

CTGGCTGCACTCTGGCGACCTGGCCTACTACGACAAGGACGGCCACTTCT

TCATCGTGGACCGGCTGAAGTCCCTGATCAAGTACCAGGGCTACCAGGTG

CCACCCGCCGAGCTGGAATCTATCCTGCTGCAGCATCCCTTCATCTTCGA

TGCCGGGGTGGCCGGCATCCCTGATGCTGATGCTGGCGAACTGCCTGCCG

CTGTGGTGGTGCTGGAAGAGGGCAAGACCATGACCGAGCAGGAAGTGATG

GACTACGTGGCCGGACAAGTGACCGCCAGCAAGAGGCTGAGAGGCGGCGT

GAAGTTCGTGGACGAGGTGCCAAAGGGCCTGACAGGCAAGATCGACAGCC

GGAAGATCCGCGAGATGCTGACAATGGGCAAGAAAAGCAAGCTGTGA

SfRE1 Luciferase
(Sequence No. 2)
ATGGCCAGCAGCATGATGAGCAAGAAGGACCTGGAAGATAAGAACGTGGT

GCACGGCCCCGACCCCTACTACCTGGTGGATGAGGGCAATGCCGGCCAGC

AGCTGCACAAGACCATCCTGAGATACGCCCAGCTGCCCGACACAATCGCC

TTCACCGACGGCCACACCAAGCGGGATGTGACCTACGCCCACTACTTCGA

CCTGACCTGCAGACTGGCCGAGAGCCTGAAGAGATACGCCCTGAACCTGC

AGAGCCGGATCGCCGTGTGCAGCGAGAACAACGTGGAATTTTTCATCCCC

GTGGTGGCCAGCCTGTACCTGGGAGTGGGAGTGGCCCCCACCAACGACAT

CTACAACGAGACAGAGCTGTTCAACAGCCTGAACATCAGCCAGCCCACCA

TCGTGTTCGTGTCCAAGCGGGCCCTGCACAAGATCCTGGAAGTGAAGAAG

CGCATCCCCATCATCAAGACCGTGGTGGTGCTGGACACCGAAGAGGACTT

CATGGGCTACCACTGCCTGCACAGCTTTATGAAGCACTACCTGCCCCCCA

ACTTCGACATCATGAGCTACAAGCCCGAAGAGTTCGCCCGGGATGGACAG

CTGGCCCTGATCATGAACAGCAGCGGCAGCACCGGCCTGCCTAAAGGCGT

GATGCTGGCCCACAGATCCGTGGTCGTGCGGTTCAGCCACTGCAAGGACC

CCGTGTTCGGCAACCAGATCATCCCCGACACCGCTATCCTGACCGTGATC

CCTTTCCACCACGGCTTCGGCATGTTCACCACCCTGGGCTACCTGACCTG

TGGCTTCCGGATCGTGCTGCTGCGGAAGTTCGACGAGCACTACTTTCTGA

AGTGCCTGCAGGACTACAAGATCCAGTTTGCCCTGCTGGTGCCTACCCTG

TTCAGCTTCTTCGCCAAGAGCACCCTGGTGGACCAGTACGACCTGAGCAA

CCTGAAAGAGATCGCCAGCGGCGGAGCCCCCCTGGCTAAAGAAGTGGGAG

AGGCCGTCGCCAAGCGGTTTAAGCTGCCCGGCATCAGACAGGGCTACGGC

CTGACCGAGACAACCAGCGCCGTGATCATCACCCCCGAGGGCGAGGATAA

GCCTGGCTCTACAGGCAAGGTGGTGCCATTCTTCAGCGCCAAGATCGTGG

ACCTGAACAGCGGCAAGAGCGTGGGCCCTCACCAGAGGGGAGAACTCTAC

CTGAAGGGCGACATGATCATGATGGGCTACTGCAACAACAAGGCCGCCAC

CGACGAGATGATCGACAAGGATGGCTGGCTGCACTCCGGCGACGTTGCCT

ACTACGACGAGGACGGCCACTTCTTCATCGTGGACCGGCTGAAGTCCCTG

ATCAAGTACAAGGGCTACCAGGTGGCCCCTGCCGAACTGGAAGCTGTGCT

GCTGCAGCATCCCTGCATCTTCGATGCCGGCGTGACCGGCGTGCCAGATG

ATGTGGACGGCGAACTGCCTGGCGCCTGTGTGGTCCTGGAAAAGGGCAAG

CACGTGACCGAGCAGGAAGTGATGGACTACGTGCCCGGCCAGCTGAGCTG

CTACAAGAGACTGAGAGGCGGTGTGCGCTTCATCGATGAGATCCCTAAGG

GCCTGACCGGCAAGATCGACCGGAAGGCCCTGAAAGAAATCCTGAAGAAA

CCCCAGAGCAAGATGTGA

1-2. Gene Introduction and Cell Culture

The human peripheral blood mononuclear cell (PBMC; manufactured by Cellular Technology Ltd.) was thawed; then, this was cultured by using a culture medium added with IL3, IL6, SCF, TPO, Flt3-Ligand, and CSF (AK02; manufactured by Ajinomoto Co., Inc.). The cell culture was conducted by using a 24-well culture plate. The cell was inoculated with the density of $2.5 \times 10^6$ cells/well, and cultured under the environment of 5% $CO_2$ at 37° C. for 7 days without changing the culture medium.

After 7 days of culturing, "the modified vector set" was introduced into PBMC by electroporation using Amaxa (manufactured by Lonza Ltd.).

Next, the PBMC having the vector introduced thereto was inoculated to the 6-well culture plate that was previously coated with a coating material (iMatrix, manufactured by Nippi Inc.); then, this was cultured in the culture medium added with IL3, IL6, SCF, TPO, Flt3-Ligand, and CSF (AK02; manufactured by Ajinomoto Co., Inc.) under the environment of 5% $CO_2$ at 37° C. for one overnight. The inoculation density of $2.0 \times 10^6$ cells/well was used.

The next day and thereafter, namely, two days after introduction of the vector and thereafter, the culturing was continued by changing 1.5 mL of the culture medium (AK02; manufactured by Ajinomoto Co., Inc.) every other day. The iPS cell-like colony was formed 8 days after introduction of the vector; then, the luminescence observation was conducted on the 12th day.

1-3. Acquisition of Images

The bright field image and the luminescent image of two colonies were acquired at the time after 12 days of culturing. The luminescence due to the catalytic action of luciferase was observed by adding luciferin with final concentration of 1 mM into the culture medium.

For acquisition of the luminescent image, the luminescent microscope LV 200 (manufactured by Olympus Corp.) was used. ImagEM (Hamamatsu Photonics K.K.) was used as the CCD camera. The capturing conditions with the exposure period of 5 minutes, the binning of 1×1, and the EM-gain of 1,200 were used. The objective lens with the magnification of 4 or 20 was used.

The luminescence due to expression of the SfRE1 luciferase was dispersed by using the filter that transmits the light of 515 to 560 nm (515-560 HQ). The luminescence due to expression of the Oki_mut1 luciferase was dispersed by using the filter that transmits the light of 610 nm (610ALP).

Figure 11:
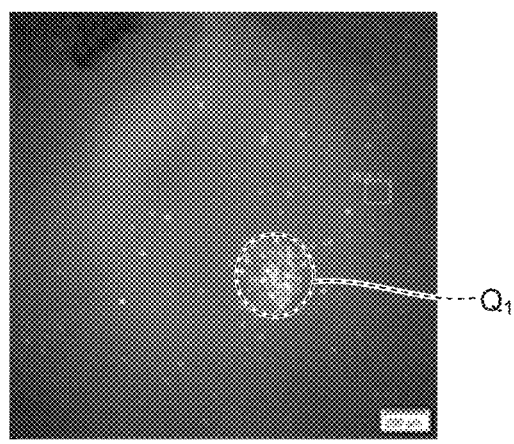
FIG. 11 is a bright field image of Example 1.
Figure 12:
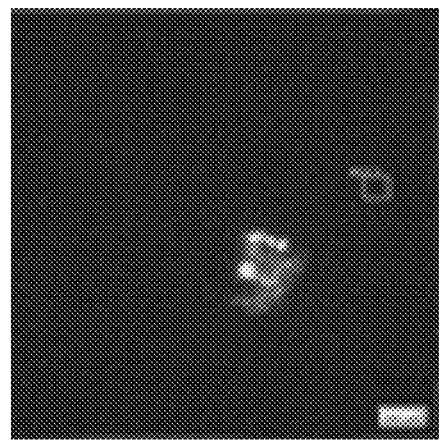
FIG. 12 is a luminescent image of the first luminescent protein in Example 1.
Figure 13:
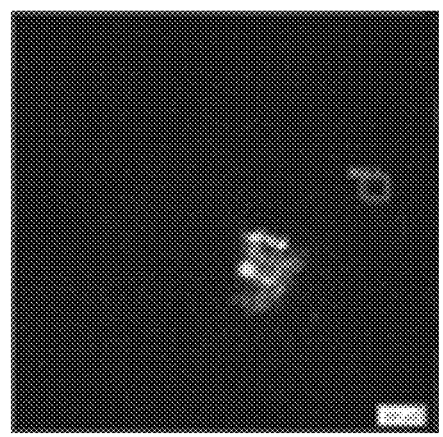
FIG. 13 is a luminescent image of the second luminescent protein in Example 1.

FIG. 11 is the bright field image of Example 1. FIG. 12 is the luminescent image of the first luminescent protein (SfRE1 luciferase) in Example 1. FIG. 13 is the luminescent image of the second luminescent protein (Oki_mut1 luciferase) in Example 1.

In the bright field image (FIG. 11), it can be seen that the colony is formed by gathering a plurality of the cells around the right and lower side of the image. In the luminescent image, it can be seen that the luciferase emits the luminescent light in the location where the colony is formed in the bright field image.

Figure 14:
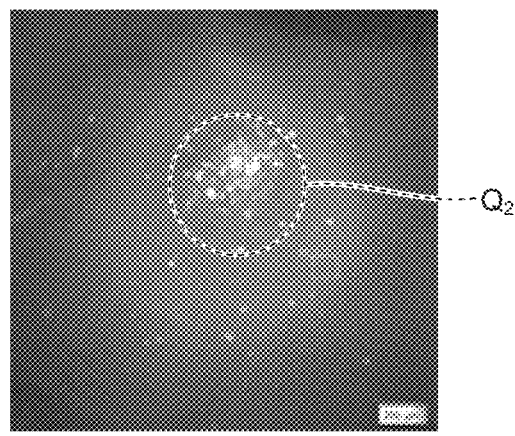
FIG. 14 is a bright field image of Example 2.
Figure 15:
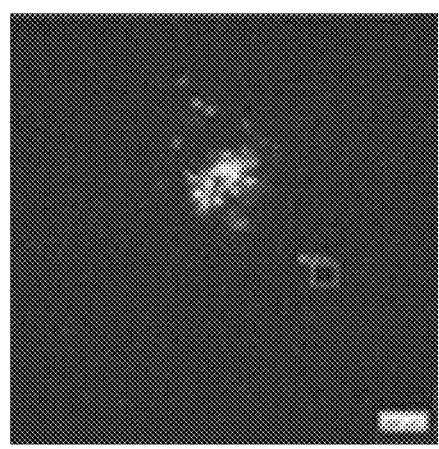
FIG. 15 is a luminescent image of the first luminescent protein in Example 2.
Figure 16:
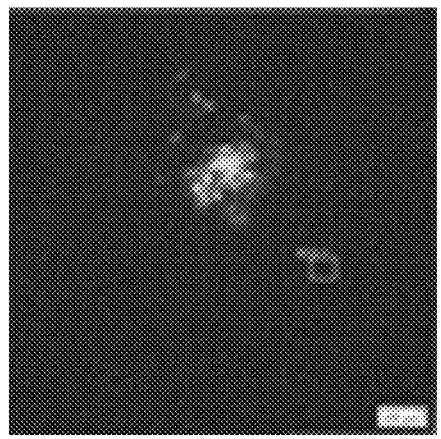
FIG. 16 is a luminescent image of the second luminescent protein in Example 2.

FIG. 14 is the bright field image of Example 2. FIG. 15 is the luminescent image of the first luminescent protein (SfRE1 luciferase) in Example 2. FIG. 16 is the luminescent image of the second luminescent protein (Oki_mut1 luciferase) in Example 2.

In the bright field image (FIG. 141), it can be seen that the colony is formed by gathering a plurality of the cells around the right and lower side of the image. In the luminescent image, it can be seen that the luciferase emits the luminescent light in the location where the colony is formed in the bright field image.

In the selection process thereafter based on the luminescence amounts (luminescence amounts of the SfRE1 luciferase and of the Oki_mut1 luciferase), the colony in Example 1 was selected as the cell capable of becoming the good iPS cell. On the other hand, the colony in Example 2 was not selected and thereby dropped out as the cell capable of becoming the good iPS cell at the time of quality judgement at the time of the third transplanting.

In the colony in Example 1 (see FIG. 11), the area $Q_1$ is recognized as the external shape of the colony. In the colony in Example 2 (see FIG. 14), the area $Q_2$ is recognized as the external shape of the colony. When comparing the area $Q_1$ with the area $Q_2$, the area $Q_2$ is larger than $Q_1$; and thus according to the conventional method to judge good/bad of the iPS cell on the basis of the external shape of the colony, the colony in Example 2 is preferentially selected. However, in the present Examples, the colony in Example 1 was selected as the cell capable of becoming the good iPS cell. As apparent from this result, it can be seen that when the cell capable of becoming the good iPS cell is selected on the basis of the luminescence amounts of a plurality of the luminescent proteins emitting the luminescent light with different initializing factors, the good iPS cell can be selected more precisely than the selection based on the size and the like of the colony.

1-4. Confirmation of Residue of Episomal Vector

By using, as the template, the genome DNA of the iPS cell selected by the process described above, the PCR was conducted under the condition described below to confirm the residue of the episomal vector.

Primer
  First primer (pEP4-SF1): TTC CAC GAG GGT AGT GAA CC
  Second primer (pEP4-SR1): TCG GGG GTG TTA GAG ACA AC PCR condition The thermal denaturation was conducted at 94° C. for 2 minutes; then, the thermal denaturation at 94° C. for 20 seconds, the annealing at 64° C. for 20 seconds, and the elongation reaction at 72° C. for 40 seconds were repeated 30 cycles; then, the elongation reaction was conducted at 72° C. for 3 minutes (reference: Yu J. et al., "Human induced pluripotent stem cells free of vector and transgene sequences", Science 324, 797-801 (2009)).

After the PCR reaction, existence of the band originated from the episomal vector was checked by electrophoresis using an agarose gel, but no band was observed. As a result, it can be said that the episomal vector was removed in the selected iPS cell, and that there is no residue of the introduced gene.

The selection method of the iPS cell and preparation method of the iPS cell as explained above can contribute to selection of usable various cells, not to mention that these can be used in the biological material for the regenerative medicine such as the iPS cell.

The selection method of the iPS cell and preparation method of the iPS cell according to the disclosure are useful to select a good iPS cell highly efficiently and precisely.

According to the disclosure, there is an advantageous effect that a good iPS cell can be selected highly efficiently and precisely.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

Sequence Listing Free Text
Sequence No. 1 Oki_mut1 Luciferase
Sequence No. 2 SfRE1 Luciferase
Sequence No. 3 First primer (pEP4-SF1)
Sequence No. 4 Second primer (pEP4-SR1)

What is claimed is:

1. A selection method of an iPS cell, the selection method comprising:
   at a reprogramming process to culture a cell including a plurality of combinations of initializing factors labelled with luminescent genes that are different with each other, acquiring a photon number per unit area or a photon number per unit time of each of the luminescent genes of the cell;
   judging whether the acquired photon number is more than a threshold that is predetermined for the acquired photon number; and
   when the acquired photon number is more than the threshold, selecting this cell as an objective cell for a next process.

2. The selection method of an iPS cell according to claim 1, wherein in a captured image of the cell including the initializing factors, the photon number is calculated by using brightness information of a prescribed area including a barycentric position of an external shape that forms a group of the cell.

3. The selection method of an iPS cell according to claim 1, wherein the judging includes classifying a probability to select a plurality of good iPS cells in a descendent order that is configured in accordance with the threshold.

4. The selection method of an iPS cell according to claim 1, wherein at the reprogramming process, the cell including, as the initializing factors, a plurality of transcription factors selected from a transcription factor group consisting of Oct3/4, Sox2, Klf4, L-myc, and LIN28 is cultured.

5. The selection method of an iPS cell according to claim 4, wherein at the reprogramming process, the cell including L-myc and LIN28 is cultured.

6. The selection method of an iPS cell according to claim 4, wherein at the reprogramming process, the cell including Sox2, Klf4, and L-myc is cultured.

7. The selection method of an iPS cell according to claim 4, wherein in a combination of a photon number of L-myc and LIN28 and a photon number of Sox2 and Klf4, a threshold to the photon number of L-myc and LIN28 is set to $1.72 \times 10^{-1}$ photons/μm$^2$/sec, and a threshold to the photon number of Sox2 and Klf4 is set to $3.59 \times 10^{-1}$ photons/μm$^2$/sec.

8. The selection method of an iPS cell according to claim 7, wherein the threshold to the photon number of L-myc and LIN28 is set to $2.30 \times 10^{-1}$ photons/μm$^2$/sec.

9. The selection method of an iPS cell according to claim 4, wherein in a combination of the photon number of L-myc and LIN28 and a photon number of Oct4, a threshold to the photon number of L-myc and LIN28 is set to $9.79 \times 10^{-1}$ photons/μm$^2$/sec, and a threshold to the photon number of Oct4 is set to $5.93 \times 10^{-1}$ photons/μm$^2$/sec.

10. The selection method of an iPS cell according to claim 9, wherein the threshold to the photon number of L-myc and LIN28 is set to 5.68 photons/μm$^2$/sec, and the threshold to the photon number of Oct4 is set to $7.25 \times 10^{-1}$ photons/μm$^2$/sec.

11. A preparation method of an iPS cell, the preparation method comprising:
    at a reprogramming process to culture a cell including a plurality of combinations of initializing factors labelled with luminescent genes that are different with each other, acquiring a luminescence amount of each of the luminescent genes of the cell;
    judging whether the acquired luminescence amount is more than a threshold that is predetermined for the acquired luminescence amount;
    when the acquired luminescence amount is more than the threshold, selecting this cell as an objective cell for a next process; and
    transplanting the selected cell to a new culture vessel, repeatedly up to a prescribed number of times.

12. The preparation method of an iPS cell according to claim 11, wherein the selecting of the cell is conducted before a first transplanting to a culture vessel.

13. The preparation method of an iPS cell according to claim 12, wherein
    a first captured image of the cell is acquired before the cell is transplanted, and
    a second captured image of the cell is acquired after the cell is transplanted to a new culture vessel, and then the cell appearing in the first captured image and the cell appearing in the second captured image are identified.

14. The preparation method of an iPS cell according to claim 11, wherein the selecting of the cell is conducted after transplanting is repeated for a prescribed number of times.

15. The preparation method of an iPS cell according to claim 11, wherein the selecting of the cell is conducted at different points of time in a same culture period or respective points of time in different transplanting periods.

16. The preparation method of an iPS cell according to claim 15, wherein a first luminescence amount acquired at a prescribed point of time before a first transplanting to a culture vessel and a luminescence amount acquired at a subsequent point of time that is different from the prescribed point of time are acquired, and then, the selecting is conducted by using a compensated luminescence amount that is the second luminescence amount compensated with a reduced amount from the first luminescence amount.

17. A control device comprising a processor comprising hardware, the processor being configured to:
    acquire, at a reprogramming process to culture a cell including a plurality of combinations of initializing factors labelled with luminescent genes that are different with each other, a photon number per unit area or a photon number per unit time of each of the luminescent genes of the cell;
    judge whether the acquired photon number is more than a threshold that is predetermined for the acquired photon number; and
    when the acquired photon number is more than the threshold, select this cell as an objective cell for a next process.

\* \* \* \* \*

SEQUENCE LISTING

<160> NUMBER OF SEQ ID NOS: 4

<210> SEQ ID NO 1
<211> LENGTH: 1647
<212> TYPE: DNA
<213> ORGANISM: Artificial Sequence
<220> FEATURE:
<223> OTHER INFORMATION: Oki_mut1 Luciferase

<400> SEQUENCE: 1

```
atggaagatg accacaagaa catcgtgcac ggccctgccc cattctaccc cctggaagag     60
ggaacagccg cgagcagct gcaccgggcc atgaagagat atgcccaggt gcccggcaca    120
atcgccttca ccgatgccca cgtggaagtg aacatcacct acagcgagta cttcgagatg    180
gcctgccggc tggccgagac aatgaagcgc tatggcctgg cctgcagca ccacattgcc    240
gtgtgcagcg agaacagcct gcagttcttc atgcccgtgt gtggcgccct gttcatcgga    300
gtgggagtgg cccccaccaa cgacatctac aacgagagag agctgtacaa cagcctgagc    360
atcagccagc ccaccatcgt gttctgcagc aagcgggccc tgcagaaaat cctgggcgtg    420
cagaaaaagc tgcccgtgat cgagaagatc gtgatcctgg acagccgcga ggactacatg    480
ggcaagcaga gcatgtacag cttcatcgag agccatctgc ccgctggctt caacgagtac    540
gactacgtgc ccgacacctt cgacagagag acagccaccg ccctgatcat gaacagcagc    600
ggctctaccg gcctgcccaa gggcgtggaa ctgacccaca gaatgtgtg cgtgcggttc    660
agccactgcc gggaccctgt gttcggcaac cagatcatcc ccgacaccgc tatcctgacc    720
gtgatccct tccaccacgg cttcggcatg ttcaccaccc tgggctacct gacctgcggc    780
ttccggatcg tgctgatgta cagattcgag gaagaactgt tcctgcggag cctgcaggac    840
tacaagatcc agagcgccct gctggtgcct accctgttca gcttcttcgc caagagcacc    900
ctggtggata gtacgacct gagcaacctg cacgagatcg cctctggcgg agccccctg    960
gctaaagaag tgggagaggc cgtggccaag cggttcaagc tgcctggcat cagacagggc   1020
tacgcctga ccgagacaac ctctgccgtg atcatcaccc caggggcga cgataagcct   1080
ggcgcctgtg gaaaggtggc cccattttc agcgccaaga ttgtggacct ggacaccagc   1140
aagacactgg gcgtgaacca gagggcgag ctgtgtctga agggcccat gattatgaag   1200
ggctacgtga caaccccga ggccaccaat gccctgatca caaggatgg ctggctgcac   1260
tctggcgacc tggcctacta cgacaaggac ggccacttct tcatcgtgga ccggctgaag   1320
tccctgatca agtaccaggg ctaccaggtg ccacccgccg agctggaatc tatcctgctg   1380
cagcatccct tcatcttcga tgccggggtg gccggcatcc ctgatgctga tgctggcgaa   1440
ctgcctgccg ctgtggtggt gctggaagag ggcaagacca tgaccgagca ggaagtgatg   1500
gactacgtgg ccggacaagt gaccgccagc aagaggctga gggcggcgt gaagttcgtg   1560
gacgaggtgc caagggcct gacaggcaag atcgacagcc ggaagatccg cgagatgctg   1620
acaatgggca agaaaagcaa gctgtga                                        1647
```

<210> SEQ ID NO 2
<211> LENGTH: 1668
<212> TYPE: DNA

<213> ORGANISM: Artificial Sequence
<220> FEATURE:
<223> OTHER INFORMATION: SfRE1 Luciferase

<400> SEQUENCE: 2

```
atggccagca gcatgatgag caagaaggac ctggaagata agaacgtggt gcacggcccc      60
gaccccctact acctggtgga tgagggcaat gccggccagc agctgcacaa gaccatcctg     120
agatacgccc agctgcccga cacaatcgcc ttcaccgacg ccacaccaa gcgggatgtg       180
acctacgccc actacttcga cctgacctgc agactggccg agagcctgaa gagatacggc     240
ctgaacctgc agagccggat cgccgtgtgc agcgagaaca cgtggaattt tttcatcccc     300
gtggtggcca gcctgtacct gggagtggga gtggccccca ccaacgacat ctacaacgag     360
acagagctgt tcaacagcct gaacatcagc cagcccacca tcgtgttcgt gtccaagcgg     420
gccctgcaca agatcctgga agtgaagaag cgcatcccca tcatcaagac cgtggtggtg     480
ctggacaccg aagaggactt catgggctac cactgcctgc acagctttat gaagcactac     540
ctgcccccca acttcgacat catgagctac aagcccgaag agttcgcccg ggatggacag     600
ctggccctga tcatgaacag cagcggcagc accggcctgc ctaaaggcgt gatgctggcc     660
cacagatccg tggtcgtgcg gttcagccac tgcaaggacc ccgtgttcgg caaccagatc     720
atccccgaca ccgctatcct gaccgtgatc cctttccacc acggcttcgg catgttcacc     780
accctgggct acctgacctg tggcttccgg atcgtgctgc tgcggaagtt cgacgagcac     840
tactttctga gtgcctgca ggactacaag atccagtttg ccctgctggt gcctaccctg     900
ttcagcttct tcgccaagag cacccctggtg gaccagtacg acctgagcaa cctgaaagag    960
atcgccagcg gcggagcccc cctggctaaa gaagtgggag aggccgtcgc caagcggttt    1020
aagctgcccg gcatcagaca gggctacggc ctgaccgaga caaccagcgc cgtgatcatc    1080
accccgagg gcgaggataa gcctggctct acaggcaagg tggtgccatt cttcagcgcc    1140
aagatcgtgg acctgaacag cggcaagagc gtgggccctc accagagggg agaactctac    1200
ctgaagggcg acatgatcat gatgggctac tgcaacaaca aggccgccac cgacgagatg    1260
atcgacaagg atggctggct gcactccggc gacttgcct actacgacga ggacggccac    1320
ttcttcatcg tggaccggct gaagtccctg atcaagtaca agggctacca ggtggcccct    1380
gccgaactgg aagctgtgct gctgcagcat ccctgcatct tcgatgccgg cgtgaccggc    1440
gtgccagatg atgtggacgg cgaactgcct ggcgcctgtg tggtcctgga aaagggcaag    1500
cacgtgaccg agcaggaagt gatggactac gtcgccggcc agctgagctg ctacaagaga    1560
ctgagaggcg gtgtgcgctt catcgatgag atccctaagg gcctgaccgg caagatcgac    1620
cggaaggccc tgaagaaat cctgaagaaa ccccagagca agatgtga                  1668
```

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ttccacgagg gtagtgaacc                                                  20

<210> SEQ ID NO 4
<211> LENGTH: 20
<212> TYPE: DNA
<213> ORGANISM: Artificial Sequence

```
<220> FEATURE:
<223> OTHER INFORMATION: Primer

<400> SEQUENCE: 4 tcggggggtgt tagagacaac                                                    20
```